United States Patent [19]

Ehrenfreund et al.

[11] Patent Number: 5,066,667
[45] Date of Patent: Nov. 19, 1991

[54] THIOXOTETRAZOLINES AND INSECTICIDAL USE THEREOF

[75] Inventors: Josef Ehrenfreund, Allschwil; Erich Stamm, Huttil, both of Switzerland

[73] Assignee: Ciba-Geigy Corporation, Ardsley, N.Y.

[21] Appl. No.: 539,755

[22] Filed: Jun. 18, 1990

[30] Foreign Application Priority Data

Jun. 26, 1989 [CH] Switzerland .................. 2369/89

[51] Int. Cl.$^5$ ............... C07D 257/04; A01N 43/713
[52] U.S. Cl. ......................... 514/381; 548/251
[58] Field of Search ................. 548/251; 514/381

[56] References Cited

U.S. PATENT DOCUMENTS

| | | | |
|---|---|---|---|
| 4,328,247 | 5/1982 | Drabek | 424/326 |
| 4,404,225 | 9/1983 | Boger et al. | 424/322 |
| 4,734,433 | 3/1988 | Drabek | 514/508 |
| 4,826,529 | 5/1989 | Covey et al. | 548/251 |
| 4,866,079 | 9/1989 | Boger | 514/346 |
| 4,885,025 | 12/1989 | Theodoridis | 548/251 |
| 4,897,424 | 1/1990 | Boger | 541/638 |
| 4,956,469 | 9/1990 | Convey et al. | 548/251 |
| 4,963,550 | 10/1990 | Boger | 514/249 |
| 4,965,389 | 10/1990 | Ehrenfreund | 558/104 |
| 4,968,720 | 11/1990 | Ehrenfreund | 514/638 |

FOREIGN PATENT DOCUMENTS

| | | |
|---|---|---|
| 0145328 | 6/1985 | European Pat. Off. . |
| 0146279 | 6/1985 | European Pat. Off. . |
| 1447662 | 12/1968 | Fed. Rep. of Germany . |
| 87/03873 | 7/1987 | PCT Int'l Appl. . |

OTHER PUBLICATIONS

Chem. Ber. 118,526–540 (1985).
J. Org. Chem., vol. 41, 10, (1976) 1875–6.
Z. Chem. 1974, 14(1), 16–17 (Ger).

Primary Examiner—David B. Springer
Attorney, Agent, or Firm—Kevin T. Mansfield; Edward McC. Roberts

[57] ABSTRACT

Novel 1-phenyl-5-thioxo-2-tetrazolines of formula I

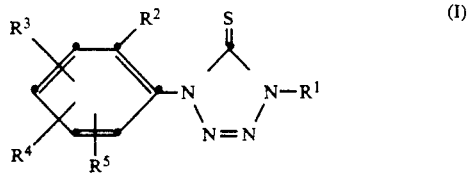

in which $R^1$ is $C_1$–$C_8$alkyl, $C_3$–$C_6$alkenyl, $C_3$–$C_6$alkynyl, $C_3$–$C_6$cycloalkyl, $C_5$–$C_6$-cycloalkenyl, $C_1$–$C_4$alkyl- or halo-substituted $C_3$–$C_6$cycloalkyl, $C_1$–$C_4$-alkyl- or halo-substituted $C_5$–$C_6$cycloalkenyl, halo-, $C_1$–$C_4$alkoxy- or phenyl-substituted $C_3$–$C_6$alkenyl, halo-, $C_1$–$C_4$alkoxy- or phenyl-substituted $C_3$–$C_8$alkynly, or $C_1$–$C_8$alkyl that is substituted by halogen, $C_1$–$C_4$alkoxy, $C_1$–$C_4$alkylthio, $C_1$–$C_4$alkoxycarbonyl, $C_3$–$C_6$cycloalkyl, phenyl, cyano, hydroxy, halophenyl, $C_1$–$C_4$alkylphenyl or by a heteroaromatic radical.

$R^2$ is $C_1$–$C_6$alkyl, $C_2$–$C_6$alkenyl, $C_2$–$C_6$alkynyl, $C_3$–$C_6$cycloalkyl, cyclopentenyl or cyclohexenyl, or is $C_1$–$C_6$alkyl that is substituted by halogen, by $C_1$–$C_4$alkoxy or by $C_1$–$C_4$alkylthio, each of $R^3$ and $R^4$, independently of the other, is hydrogen, halogen, $C_1$–$C_4$alkyl, $C_1$–$C_4$haloalkyl, $C_1$–$C_4$alkoxy, $C_1$–$C_4$alkylthio, $C_3$–$C_6$-cycloalkyl, $C_2$–$C_4$alkenyl, $C_2$–$C_4$alkynyl, $C_2$–$C_6$alkoxyalkyl, $C_2$–$C_6$alkylthioalkyl, $C_1$–$C_4$cyanoalkyl, phenyl-$C_2$–$C_4$alkenyl or phenyl-$C_2$–$C_4$alkynyl, or $R^3$ and $R^4$ together are —CH=CH—CH=CH—, —CH$_2$—CH=CH—, —(CH$_2$)$_4$—, —(CH$_2$)$_4$—, —(CH$_2$)$_3$—, —O—CH$_2$—O—, —O—CH$_2$—CH$_2$—O—, —CH$_2$—O—CH$_2$—, —(CH$_2$)—O—CH$_2$—, —(CH$_2$)$_2$—CH=CH— or —CH$_2$—CH=CH—CH$_2$— bridge, each of which may be substituted by one or two $C_1$–$C_4$alkyl groups, and $R^5$ is hydrogen or a —Z—$R^6$ group in which $R^6$ is phenyl, naphthyl or pyridyl, or is phenyl, naphthyl or pyridyl each of which is substituted by one or two substituents from the group halogen, $C_1$–$C_4$alkyl, $C_1$–$C_4$alkoxy, $C_1$–$C_4$haloalkoxy, $C_1$–$C_4$haloalkyl, $C_1$–$C_4$alkylthio, $C_1$–$C_4$haloalkylthio, di-$C_1$–$C_4$alkylamino, nitro cyano $C_1$–$C_4$alkoxycarbonyl and $C_1$–$C_4$alkylcarbonyl and Z is oxygen, sulfur, a direct bond, —NH—, —N($C_1$–$C_2$alkyl)—, —N(CHO—, —CH$_2$—, —CH(CH$_3$)— or —C(CH$_3$)$_2$— can be used as pesticides. Preferably, insects and arachnids can be controlled.

15 Claims, No Drawings

THIOXOTETRAZOLINES AND INSECTICIDAL USE THEREOF

The present invention relates to novel substituted 1-phenyl-5-thioxo-2-tetrazolines, to processes and intermediates for the preparation thereof, to pesticidal compositions containing those compounds, and to the use thereof in the control of pests.

The 1-phenyl-5-thioxo-2-tetrazolines according to the invention correspond to formula I

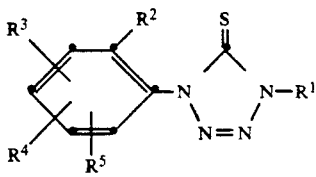

in which
$R^1$ is $C_1$–$C_8$alkyl, $C_3$–$C_6$alkenyl, $C_3$–$C_6$alkynyl, $C_3$–$C_6$-cycloalkyl, $C_5$–$C_6$-cycloalkenyl, $C_1$–$C_4$alkyl- or halo-substituted $C_3$–$C_6$cycloalkyl, $C_1$–$C_4$-alkyl- or halo-substituted $C_5$–$C_6$cycloalkyl, halo-, $C_1$–$C_4$alkoxy- or phenyl-substituted $C_3$–$C_6$alkenyl, halo-, $C_1$–$C_4$alkoxy- or phenyl-substituted $C_3$–$C_8$alkynyl, or $C_1$–$C_8$alkyl that is substituted by halogen, $C_1$–$C_4$alkoxy, $C_1$–$C_4$alkylthio, $C_1$–$C_4$alkoxycarbonyl, $C_3$–$C_6$cycloalkyl, phenyl, cyano, hydroxy, halophenyl, $C_1$–$C_4$alkylphenyl or by a hetero-aromatic radical, $R^2$ is $C_1$–$C_6$alkyl, $C_2$–$C_6$alkenyl, $C_2$–$C_6$alkynyl, $C_3$–$C_6$-cycloalkyl, cyclopentenyl or cyclohexenyl, or is $C_1$–$C_6$alkyl that is substituted by halogen, by $C_1$–$C_4$alkoxy or by $C_1$–$C_4$alkylthio, each of $R^3$ and $R^4$, independently of the other, is hydrogen, halogen, $C_1$–$C_4$alkyl, $C_1$–$C_4$haloalkyl, $C_1$–$C_4$alkoxy, $C_1$–$C_4$alkylthio, $C_3$–$C_6$cyclo-alkyl, $C_2$–$C_4$alkenyl, $C_2$–$C_4$alkynyl, $C_2$–$C_6$alkoxyalkyl, $C_2$–$C_6$alkylthioalkyl, $C_1$–$C_4$cyanoalkyl, phenyl-$C_2$–$C_4$alkenyl or phenyl-$C_2$–$C_4$alkynyl, or $R^3$ and $R^4$ together are a —CH=CH—CH=CH—, —CH$_2$—CH=CH—, —(CH$_2$)$_4$—, —(CH$_2$)$_3$—, —O—CH$_2$—O—, —O—CH$_2$—CH$_2$—O—, —CH$_2$—O—CH$_2$—, —(CH$_2$)$_2$—CH=CH— or —CH$_2$—CH=CH—CH$_2$— bridge, each of which may be substituted by one or two $C_1$–$C_4$alkyl groups, and $R^5$ is hydrogen or a —Z—$R^6$ group in which
$R^6$ is phenyl, naphthyl or pyridyl, or is phenyl, naphthyl or pyridyl each of which is substituted by one or two substituents from the group halogen, $C_1$–$C_4$alkyl, $C_1$–$C_4$alkoxy, $C_1$–$C_4$haloalkoxy, $C_1$–$C_4$haloalkyl, $C_1$–$C_4$alkylthio, $C_1$–$C_4$haloalkylthio, di-$C_1$–$C_4$alkylamino, nitro, cyano, $C_1$–$C_4$alkoxycarbonyl and $C_1$–$C_4$alkylcarbonyl, and Z is oxygen, sulfur, a direct bond, —NH—, —N($C_1$–$C_2$alkyl)—, —N(CHO)—, —CH$_2$—, —CH(CH$_3$)— or —C(CH$_3$)$_2$—.

As a class, 1-phenyl-5-oxo- or -5-thioxo-2-tetrazolines are known from the literature to be herbicidally active or as auxiliaries for photographic materials. Compounds of the type mentioned are disclosed, for example, in DE-OS 1 447 662, DD-PS 119 322 and WO 85/01939.

The individual generic terms used in the definition of formula I according to the invention are to be understood as follows:

The halogen atoms suitable as substituents are both fluorine and chlorine atoms as well as bromine and iodine atoms, with fluorine and chlorine being preferred. Halogen in such cases is either an independent substituent or part of a substituent as in haloalkyl, haloalkoxy, haloalkylthio or halophenyl.

The alkyl, alkylthio and alkoxy radicals suitable as substituents may be straight-chain or branched. There may be mentioned as examples of such alkyl radicals methyl, ethyl, propyl, isopropyl, butyl, i-butyl, sec.-butyl, tert.-butyl or pentyl, hexyl, octyl and their isomers. Suitable alkoxy radicals are, for example: methoxy, ethoxy, propoxy, isopropoxy or butoxy and their isomers. Alkylthio is, for example, methylthio, ethylthio, isopropylthio, propylthio or the isomers of butylthio. Substituents that are composed of several generic groups, such as alkoxyalkyl or alkylthioalkyl, contain appropriate combinations of the mentioned individual substituents.

The alkenyl and alkynyl radicals suitable as substituents may be straight-chain or branched and contain one or more unsaturated bonds. It is also possible for doubly and triply unsaturated bonds to be present in the same radical. These unsaturated radicals preferably contain from two to six carbon atoms. Examples of such alkenyl and alkynyl radicals are, inter alia, vinyl, allyl, 1-propenyl, isopropenyl, allenyl, butenyls, butadienyls, hexenyls, hexanedienyl, ethynyl, 1-propynyl, 2-propynyl, butinyls, pentynyls, hexynyls, hexadiynyls and 2-penten-4-ynyl.

The phenylalkyl, phenylalkenyl and phenylalkynyl radicals suitable as substituents may be straight-chain or branched. The following, inter alia, are suitable examples: benzyl, phenethyl, phenylpropyl, phenylisopropyl, phenylbutyl and its isomers, phenylvinyl, phenylallyl, phenylbutenyl, phenylethynyl, phenylpropynyl and phenylbutynyl.

If the alkyl, alkoxy, alkylthio, alkenyl, alkynyl or phenylalkyl radicals suitable as substituents are halo-substituted, then they may be only partially halogenated or alternatively perhalogenated. The halosubstitution of the phenylalkyl radicals may be either in the phenyl nucleus or in the alkyl chain, or in both simultaneously. The above definitions for the halogen atoms, alkyl, alkoxy, alkylthio, alkenyl, alkynyl and phenylalkyl groups apply here too. Examples of the alkyl elements of these groups are: methyl mono- to tri-substituted by fluorine, chlorine and/or bromine, such as, for example, CHF$_2$ or CF$_3$; ethyl mono- to penta-substituted by fluorine, chlorine and/or bromine, such as, for example, CH$_2$CF$_3$, CF$_2$CF$_3$, CF$_2$CCl$_3$, CF$_2$CHCl$_2$, CF$_2$CHF$_2$, CF$_2$CFCl$_2$, CF$_2$CHBr$_2$, CF$_2$CHClF, CF$_2$CHBrF or CClFCHClF; propyl or isopropyl each mono- to hepta-substituted by fluorine, chlorine and/or bromine, such as, for example, CH$_2$CHBrCH$_2$Br, CF$_2$CHFCF$_3$, CH$_2$CF$_2$CF$_3$ or CH(CF$_3$)$_2$; butyl or an isomer thereof each mono- to nona-substituted by fluorine, chlorine and/or bromine, such as, for example, CF(CF$_3$)CHFCF$_3$ or CH$_2$(CF$_2$)$_2$CF$_3$; vinyl, propynyl or pentadiynyl each mono- to tri-substituted by fluorine, chlorine and/or bromine; allyl, 1-propenyl, butadienyl or a butynyl radical each mono- to penta-substituted by fluorine, chlorine and/or bromine,; a butenyl, pentadienyl or pentynyl radical each mono- to hepta-substituted by fluorine, chlorine and/or bromine; benzyl mono- to hepta-substituted by fluorine, chlorine and/or bromine; phenethyl mono- to nona-substituted by fluorine, chlorine and/or bromine; phenylpropyl or phenylisopropyl each mono- to undecasubstituted by fluorine, chlorine and/or bromine.

Cycloalkyl radicals suitable as substituents are, for example, cyclopropyl, cyclobutyl, cyclopentyl and cyclohexyl.

Examples of alkoxycarbonyl and alkylcarbonyl radicals are methoxycarbonyl, ethoxycarbonyl, propoxycarbonyl, isopropoxycarbonyl and butoxycarbonyl. Alkylcarbonyl is, for example, acetyl, propionyl, butyryl or valeryl, or an isomer thereof.

Alkylphenyl is a phenyl group substituted by an alkyl group. A hetero-aromatic radical in the definition of $R^1$ is to be understood as an aromatic ring that contains one or more hetero atoms as ring members. The following are examples: pyrrole, pyrazole, imidazole, triazoles, tetrazole, oxazoles, thiazoles, oxadiazoles, thiadiazoles, pyridine, pyrimidine, pyrazine, pyridazine, triazines and quinoline.

In the case where, as in the definition of $R^1$, certain radicals may themselves be further substituted, then those radicals contain one or more substituents, but preferably no more than two.

In the case where $R^3$ and $R^4$ together form one of the mentioned bridges, $R^3$ and $R^4$ are bonded to adjacent carbon atoms of the phenyl ring.

Among the compounds of formula I, attention is drawn to those subgroups in which a) $R^1$ is $C_1$-$C_5$alkyl, $C_3$-$C_5$alkenyl, $C_3$-$C_5$alkynyl, $C_5$-$C_6$cycloalkyl, or $C_1$-$C_4$alkyl that is substituted by $C_1$-$C_4$alkoxy, by phenyl or by cyclopropyl, or b) $R^2$ is $C_1$-$C_4$alkyl or $C_5$-$C_6$cycloalkyl, or c) each of $R^3$ and $R^4$, independently of the other, is hydrogen, $C_1$-$C_4$-alkyl, $C_2$-$C_3$alkynyl, $C_2$-$C_3$alkenyl, or $C_2$-$C_4$alkoxyalkyl, or d) $R^5$ is hydrogen, benzyl, 1-phenethyl, phenoxy, halophenoxy, phenylthio, phenyl, dichloropyridyloxy, N-formylanilinyl or N-formylhaloanilinyl.

Of the compounds of sub-group c), attention is drawn to those in which one of the substituents $R^3$ and $R^4$ is hydrogen and the other occupies the 6-position of the phenyl ring, especially those in which $R^3$ is $C_1$-$C_4$alkyl in the 6-position of the phenyl ring and $R^4$ is hydrogen.

Preferred compounds of sub-group d) are those in which $R^5$ is hydrogen, benzyl, phenoxy or halophenoxy in the 4-position of the phenyl ring.

Groups of compounds of formula I that have proved to be especially preferred are those compounds in which $R^2$ is $C_1$-$C_4$alkyl or $C_5$-$C_6$cycloalkyl, $R^3$ is $C_1$-$C_4$alkyl in the 6-position of the phenyl ring, $R^4$ is hydrogen and $R^5$ is hydrogen, benzyl, phenoxy or halophenoxy in the 4-position of the phenyl ring.

Also preferred are compounds of formula I in which $R^1$ is $C_1$-$C_5$alkyl, $C_3$-$C_5$alkenyl, $C_3$-$C_5$alkynyl, $C_5$-$C_6$-cycloalkyl, or $C_1$-$C_4$alkyl that is substituted by $C_1$-$C_4$alkoxy, by phenyl or by cyclopropyl, $R^2$ is $C_1$-$C_4$-alkyl or $C_5$-$C_6$cycloalkyl, each of $R^3$ and $R^4$, independently of the other, is hydrogen, $C_1$-$C_4$alkyl, $C_2$-$C_3$alkynyl, $C_2$-$C_3$alkenyl or $C_2$-$C_4$-alkoxyalkyl and $R^5$ is hydrogen, benzyl, 1-phenethyl, phenoxy, halophenoxy, phenylthio, phenyl, dichloropyridyloxy, N-formylanilinyl or N-formylhaloanilinyl.

A most especially outstanding group of compounds of formula I is that in which $R^1$ is $C_1$-$C_5$alkyl or $C_5$-$C_6$-cycloalkyl, $R^2$ is $C_1$-$C_4$alkyl or $C_5$-$C_6$cycloalkyl, $R^3$ is $C_1$-$C_4$alkyl in the 6-position of the phenyl ring, $R^4$ is hydrogen, and $R^5$ is hydrogen, benzyl, phenoxy or halophenoxy in the 4-position of the phenyl ring.

The following may be mentioned as preferred individual compounds of formula I:

1-(2-ethyl-6-isopropylphenyl)-4-isopropyl-5-thioxo-2-tetrazoline, 1-(2,6-diisopropyl-4-phenoxyphenyl)-4-isopropyl-5-thioxo-2-tetrazoline, 1-(2-ethyl-6-isopropylphenyl)-4-methyl-5-thioxo-2-tetrazoline, 1-(2,6-diisopropyl-4-phenoxyphenyl)-4-(2,2-dimethylpropyl)-5-thioxo-2-tetrazoline, 1-(2-cyclopentyl-6-isopropylphenyl)-4-isopropyl-5-thioxo-2-tetrazoline, 1-(2-cyclopentyl-6-isopropylphenyl)-4-sec.-butyl-5-thioxo-2-tetrazoline, 1-(2,6-diisopropyl-4-phenoxyphenyl)-4-ethyl-5-thioxo-2-tetrazoline, 1-(2,6-diisopropylphenyl)-4-(1-methyl-2-methoxyethyl)-5-thioxo-2-tetrazoline, 1-(2-methyl-6-isopropylphenyl)-4-isopropyl-5-thioxo-2-tetrazoline, 1-(2-methyl-6-isopropylphenyl)-4-(2,2-dimethylpropyl)-5-thioxo-2-tetrazoline, 1-(2,6-diisopropyl-4-phenoxyphenyl)-4-cyclopentyl-5-thioxo-2-tetrazoline, 1-(2,6-diisopropylphenyl)-4-isopropyl-5-thioxo-2-tetrazoline, 1-(2-ethyl-6-isopropylphenyl)-4-(2,2-dimethylpropyl)-5-thioxo-2-tetrazoline, 1-(2,6-diisopropylphenyl)-4-(2,2-dimethylpropyl)-5-thioxo-2-tetrazoline, 1-(2,6-diisopropylphenyl)-4-(2-cyclohexenyl)-5-thioxo-2-tetrazoline, 1-(2-methyl-6-isopropylphenyl)-4-sec.-butyl-5-thioxo-2-tetrazoline, 1-(2,6-diisopropyl-4-phenoxyphenyl)-4-cyclopropylmethyl-5-thioxo-2-tetrazoline, 1-(2,6-diisopropyl-4-benzylphenyl)-4-sec.-butyl-5-thioxo-2-tetrazoline, 1-(2,6-diisopropyl-4-benzylphenyl)-4-(2,2-dimethylpropyl)-5-thioxo-2-tetrazoline, 1-(2,6-diisopropyl-4-benzylphenyl)-4-isopropyl-5-thioxo-2-tetrazoline, 1-[2,6-diisopropyl-4-(2-fluorophenoxy)-phenyl]-4-isopropyl-5-thioxo-2-tetrazoline, 1-[2,6-diisopropyl-4-(1-phenethyl)-phenyl]-4-isopropyl-5-thioxo-2-tetrazoline, 1-(2-cyclopentyl-6-isopropyl-4-phenoxyphenyl)-4-isopropyl-5-thioxo-2-tetrazoline, 1-(2-tert.-butyl-6-methylphenyl)-4-isopropyl-5-thioxo-2-tetrazoline, 1-(2-tert.-butyl-6-methylphenyl)-4-sec.-butyl-5-thioxo-2-tetrazoline, 1-(2-tert.-butyl-6-methylphenyl)-4-(2,2-dimethylpropyl)-5-thioxo-2-tetrazoline and 1-(2,6-diethylphenyl)-4-isopropyl-5-thioxo-2-tetrazoline.

The compounds of formula I of the invention can be prepared according to processes that are known in principle, for example by a) treating a 1-phenyl-5-oxo-2-tetrazoline of formula II

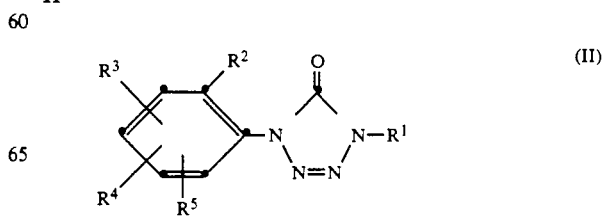

in which $R^1$, $R^2$, $R^3$, $R^4$ and $R^5$ are as defined for formula I, with a thionating agent, or b) alkylating a 1-phenyl-5-thioxo-2-tetrazoline of formula III

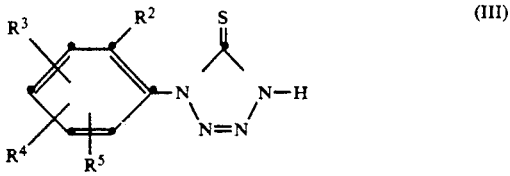 (III)

in which $R^2$, $R^3$, $R^4$ and $R^5$ are as defined for formula I, with an alkylating agent of formula IV $$X-R^{11} \quad \text{(IV)}$$

in which $R^{11}$ has the same meaning as $R^1$ in formula I or is a substituent that can be converted into $R^1$, and X is a leaving group, and converting the resulting 1-phenyl-5-mercaptotetrazole of formula V

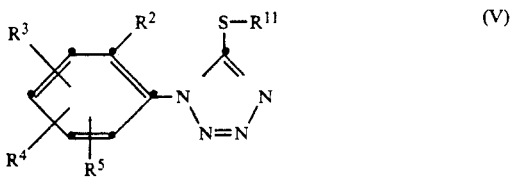 (V)

by means of a rearrangement reaction into the corresponding 1-phenyl-5-thioxo-2-tetrazoline of formula Ia

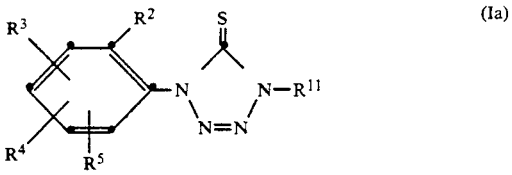 (Ia)

and, if appropriate, converting the substituent $R^{11}$ into a radical according to the definition of $R^1$, or c) alkylating a 1-phenyl-5-thioxo-2-tetrazoline of formula III in the presence of a base by reaction with an activated carbonylvinyl or cyanovinyl derivative that can be converted into the radical $R^1$ and, if desired, converting the introduced substituent into a radical according to the definition of $R^1$.

The reaction of variant a) converts the carbonyl function of the starting material of formula II directly into a thiocarbonyl function. Analogous thionation reactions are known in the literature. Analogous processes are described, for example, in Chem. Ber. 118, 526 (1985) and J. Org. Chem. 41, 1875 (1976). Process a) according to the invention is preferably carried out in the presence of an inert organic solvent. Suitable solvents are aromatic solvents, such as benzene, toluene, xylene, mesitylene, chlorobenzene, dichlorobenzene, pyridine or tetraline; chlorinated hydrocarbons, such as methylene chloride, chloroform, carbon tetrachloride, ethylene chloride, trichloroethane or tetrachloroethane; nitriles, such as acetonitrile or propionitrile or ethers such as dioxan, tetrahydrofuran or dimethylethylene glycol. The reaction temperatures are generally from +20° C. to +200° C. A range of from +60° C. to +140° C. is preferred, and attention must be drawn especially to the boiling range of the reaction mixture. The reaction according to the invention is also promoted by performing the thionation reaction using ultrasound and employing a temperature of from +20° C. to the boiling point of the mixture. The use of ultrasound sources to promote thionation reactions is described in analogous processes in J. Org. Chem. 46, 3558 (1981).

Numerous thionation agents have already been described in the literature. Most of these agents can be used in the processes according to the invention. Reagents that have proved especially favourable are O,O-diethyldithiophosphoric acid $(C_2H_5O)_2PS_2H$, boron sulfide $B_2S_3$ or $B_2S_5$, phosphorus pentasulfide $P_2S_5$ or 2,4-bis-(4-methoxyphenyl)-1,3-dithia-2,4-diphosphetane-2,4-disulfide (Lawesson's reagent).

The reaction of variant b) of the process of the invention can either be performed in two reaction steps with isolation of the intermediate of formula V, or carried out in a single process step without isolation of the intermediate. The rearrangement reaction of V to form Ia can be effected either thermally by heating, or in the presence of a suitable catalyst. Suitable rearrangement catalysts are generally complex compounds of transition metals, especially palladium complexes, such as, for example, bis-benzonitrilo-palladium chloride of the formula $Pd(C_6H_5\text{-}CN)_2Cl_2$. Process variant b) according to the invention is advantageously carried out in the presence of an inert organic solvent at the boiling temperature of the reaction mixture. Suitable solvents are amides, such as dimethylformamide or diethylformamide, aromatic solvents, such as benzene, toluene, xylene, mesitylene, chlorobenzene, dichlorobenzene, pyridine or tetraline; chlorinated hydrocarbons, such as methylene chloride, chloroform, carbon tetrachloride, ethylene chloride, trichloroethane or tetrachloroethane; nitriles, such as acetonitrile or propionitrile, or ethers, such as dioxan, tetrahydrofuran or dimethylethylene glycol.

The leaving groups X are selected from the series of leaving groups customary for nucleophilic substitution reactions. Suitable leaving groups X are preferably chlorine, bromine, iodine, toluenesulfonyloxy, methanesulfonyloxy, trifluoromethanesulfonyloxy and benzenesulfonyloxy. Substituents of the definition $R^{11}$ that can be converted into radicals of the definition $R^1$ are those radicals that can be thus converted by simple reactions, such as, for example, hydrolysis, hydrogenation or addition reactions. Examples are carbonyl group-containing radicals that are halogenated, hydrogenated or hydrolysed after the substitution, or unsaturated substituents that, for example, are converted into saturated derivatives by 1,2-addition, such as by halogen, hydrogen halide or alcohol addition.

In process variant c), there are linked with the intermediate of formula III by 1,4-addition those radicals $R^1$ that contain at least 3 carbon atoms and can be formed under the conditions of a Michael addition. The structural elements carbonylvinyl

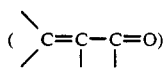

or cyanovinyl

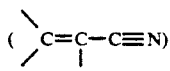

must be present as activated Michael reagents in the alkylating agents. If desired, the resulting products can be converted by conventional derivatisation reactions into different radicals $R^1$. Suitable bases for carrying out variant c) are preferably tert.-amines, such as triethylamine, pyridine or dimethylaminopyridine, but also alkali metal alcoholates or alkali metal hydrides. Advantageously process c) is carried out in an inert solvent at the boiling temperature of the reaction mixture. Such solvents are alcohols, such as methanol, ethanol, propanol or isopropanol, amides, such as dimethylformamide or diethylformamide, aromatic solvents, such as benzene, toluene, xylene, mesitylene, chlorobenzene, dichlorobenzene, pyridine or tetraline; chlorinated hydrocarbons, such as methylene chloride, chloroform, carbon tetrachloride, ethylene chloride, trichloroethane or tetrachloroethane; nitriles, such as acetonitrile or propionitrile, or ethers, such as dioxan, tetrahydrofuran or dimethylethylene glycol.

In principle it is also possible in the preparation of compounds of formula I to convert the substituents $R^1$, $R^2$, $R^3$, $R^4$ and $R^5$ by suitable derivatisation reactions or substitution reactions into different radicals within the corresponding definition. For example, a halogen substituent included under $R^3$ or $R^4$ can be replaced by a $-Z-R^6$ radical by a nucleophilic substitution reaction.

The starting materials of formula IV are known and can be obtained commercially, or they can be obtained according to processes that are known per se.

The starting compounds of formula II can be obtained according to the following Scheme 1 from known anilines of formula VI by way of isocyanates of formula VII and 1-phenyl-5-oxotetrazolines of formula VIII.

SCHEME 1

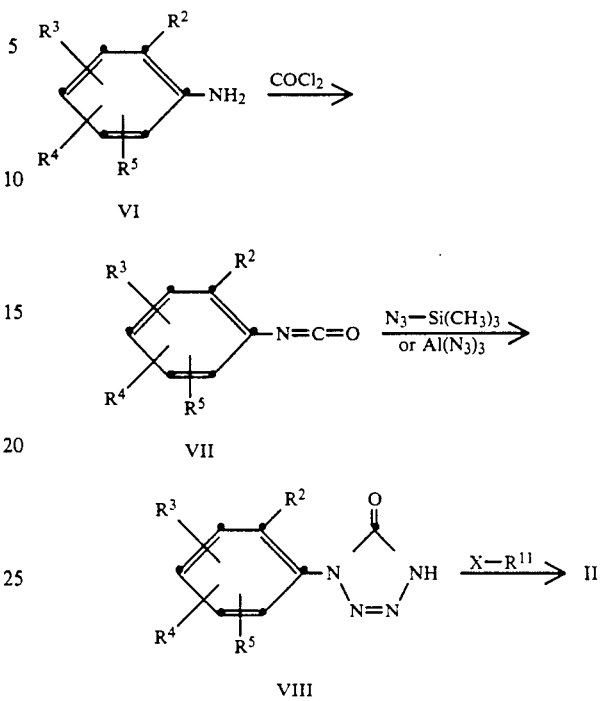

$R^2$, $R^3$, $R^4$ and $R^5$ are as defined for formula I and X and $R^{11}$ are as defined for formula IV.

The starting compounds of formula III can be obtained according to Scheme 2 from known anilines of formula VI by way of thioisocyanates of formula IX or anilinocarbodithioates of formula X.

SCHEME 2

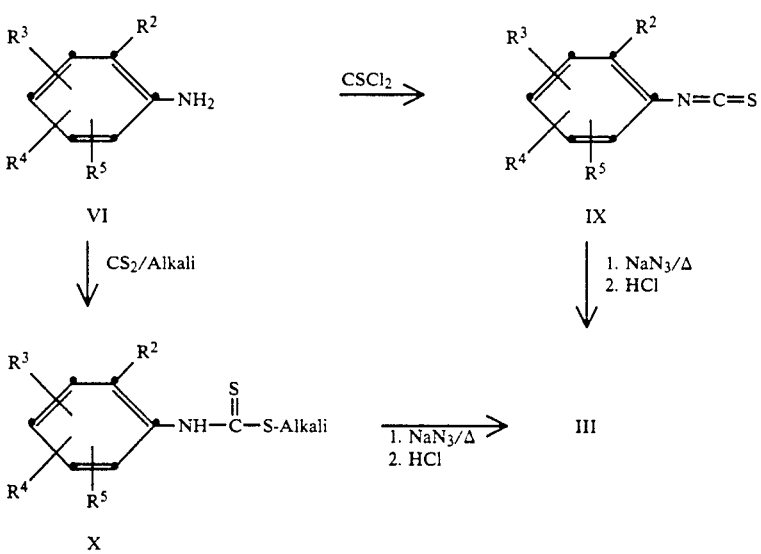

$R^2$, $R^3$, $R^4$ and $R^5$ are as defined for formula I.

The intermediates of formula III can be obtained from those of formula II also by treatment with thionating agents, such as those used for variant a) of the preparation process according to the invention.

The intermediates of formulae II and VIII are novel. They were developed specifically for the synthesis of compounds of formula I and the present invention therefore extends to them.

It has been found that whilst being well tolerated by warm-blooded animals and plants, the compounds of formula I of the invention are valuable active ingredients in the control of pests. In particular, the use of the active ingredients of the invention is directed to insects and spinning organisms that occur in useful plants and ornamentals in agriculture, especially in cotton, vegetable and fruit plantations, in forestry, in stock and material protection and also in the hygiene sector especially in connection with domestic animals and productive livestock. They are effective against all or individual stages of development of normally sensitive species and also resistant species. Their effect may manifest itself in a direct kill of the pests, or not until after some time, for example during shedding, or in a reduced oviposition and/or hatching rate. The following are included among the above-mentioned pests: of the order Lepidoptera, for example Amylois spp., Coleophora spp., Yponomeuta spp., Prays spp., Lyonetia spp., *Keiferia lycopersicella, Pectinophora gossypiella, Plutella xylostella, Leucoptera scitella*, Lithocollethis spp., Aegeria spp., Synanthedon spp., Adoxophyes spp., Pieris spp., Archips spp., Argyrotaenia spp., Choristoneura spp., Pandemis spp., Sparganothis spp., Cnephasia spp., Acleris spp., Tortrix spp., Cochylis spp., *Eupoecilia ambiguella, Hedya nubiferana, Lobesia botrana*, Eucosma spp., Cydia spp., Grapholita spp., Pammene spp., Malacosoma spp., *Manduca sexta*, Chilo spp., Diatraea spp., *Crocidolomia binotalis, Ostrinia nubilalis, Cadra cautella*, Ephestia spp., Operophtera spp., Thaumetopoea spp., Euproctis spp., Lymantria spp., Agrotis spp., Euxoa spp., *Mamestra brassicae, Panolis flammea, Busseola fusca*, Sesamia spp., Spodoptera spp., Heliothis spp., Earias spp., Autographa spp., *Trichoplusia ni, Cryptophlebia leucotreta, Phthorimaea operculella, Diparopsis castanea, Alabama argillaceae, Anticarsia gemmatalis* and *Hellula undalis*, Cnaphalocrocis spp., Scirpophage spp., *Hyphantria cunea, Carposina nipponensis, Phtorimaea operculella, Cryptophlebia leucotreta, Clysia ambiguella* and *Pieris rapae*; of the order Coleoptera, for example Sitotroga spp., *Leptinotarsa decemlineata*, Diabrotica spp., Agriotes spp., Anthonomus spp., Cosmopolites spp., Dermestes spp., Epilachna spp., Orycaephilus spp., Sitophilus spp., Otierhynchus spp., Tribolium spp., Tenebrio spp., Melolontha spp., Popillia spp., Rhizopertha spp., Trogoderma spp., Curculio spp., Eremnus spp. and Phlyctinus spp., Lissorhoptrus spp., *Chaetocnema tibialis*, Psylliodes spp., *Atomaria linearis* and Scarabeidae; of the order Orthoptera, for example Blatta spp., Periplaneta spp., *Leucophaea maderae*, Blattella spp., Gryllotalpa spp., Locusta spp. and Schistocerca spp.; of the order Isoptera, for example Reticulitermes spp.; of the order Psocoptera, for example Liposcelis spp.; of the order Anoplura, for example Phylloxera spp., Pemphigus spp., Pediculus spp., Haematopinus spp. and Linognathus spp., of the order Mallophaga, for example Trichodectes spp. and Damalinea spp.; of the order Thysanoptera, for example Hercinothrips spp., *Thrips tabaci*, Taeniothrips spp. and *Scirtothrips aurantii*, Frank Liniella spp. and *Thrips palmi*; of the order Heteroptera, for example Eurygaster spp., Dysdercus spp., Piesma spp., Cimex spp., Rhodnius spp., Triatoma spp., Nezara spp., Scotinophara spp., Leptocorisa spp., Euchistus spp., *Sahlbergella singularis* and *Distantiella theobroma*; of the order Homoptera, for example *Aleurodes brassicae, Bemisia tabaci, Trialeurodes vaporariorum*, Aphididae, Empoasca spp., Nephotettix spp., Laodelphax spp., Nilaparvata spp., Aonidiella spp., *Lecanium corni*, Saissetia spp., Aspidiotus spp., Pseudococcus spp., Planococcus spp., Pseudaulacaspis spp., Quadraspidiotus spp., Psylla spp., *Chrysomphalus aonidium, Aleurothrixus floccosus, Trioza erytreae, Eriosoma larigerum, Unaspis citri*, Ceroplaster spp. and Partatoria spp., Lepidosaphes spp., Erythroneura spp., Gascardia spp., *Coccus hesperidum, Pulvinaria aethiopica*, Schizaphis spp., Aphis spp., Sitobion spp., Macrosiphus spp., Rhopalosiphum spp., Myzus spp., Pemphigus spp., Scaphoideus spp. and *Chrysophalus dictyospermi*; of the order Hymenoptera, for example Diprion spp., Hoplocampa spp., Lasius spp., *Monomorium pharaonis*, Vespa spp., Neodiprion spp. and Solenopsis spp., Atta spp., Acromyrex, Diprionidae, *Gilpinia polytoma* and Cephus spp.; of the order Diptera, for example Aedes spp., Culex spp., *Drosophila melanogaster*, Musca spp., Fannia spp., *Calliphora erythrocephala*, Lucilia spp., Chrysomyia spp., Cuterebra spp., Glossina spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami*, Ceratitis spp., Dacus spp., Tipula spp., Liriomyza spp., Melanagromyza spp., *Antherigona soccata*, Sciara spp., *Rhagoletis pomonella* and Orseolina spp.; of the order Siphonaptera, for example *Xenopsylla cheopis* and Ceratophyllus spp.; of the order Acarina, for example Panonychus spp., Tetranychus spp., Tarsonemus spp., *Bryobia praetiosa, Acarus siro*, Argas spp., Ornithodoros spp., *Dermanyssus gallinae*, Eriophyes spp., *Phyllocoptruta oleivora*, Boophilus spp., Rhipicephalus spp., Amblyomma spp., Hyalomma spp., Ixodes spp., Psoroptes spp., Chorioptes spp., Saracoptes spp., *Aceria sheldoni, Polyphagotarsonemus latus, Eotetranychus carpini* and Brevipalpus spp., Calipitrimerus spp., *Aculus schlechtendali*, Rhizoglyphus spp. and *Olygonychus pratensis* and of the order Thysanura, for example *Lepisma saccharina*.

The good pesticidal activity of the compounds of formula I of the invention corresponds to a death rate (mortality) of at least 50-60% of the pests mentioned.

The activity of the compounds of the invention and of the compositions containing them can be substantially broadened and adapted to the prevailing circumstances by the addition of other insecticides and/or acaricides. Examples of suitable additives are representatives of the following classes of active substances: organophosphorus compounds, nitrophenols and derivatives thereof, formamidines, ureas, carbamates, pyrethroids, chlorinated hydrocarbons and *Bacillus thuringiensis* preparations.

The compounds of formula I are used in unmodified form or, preferably, together with the adjuvants conventionally employed in the art of formulation, and can therefore be formulated in known manner e.g. into emulsifiable concentrates, directly sprayable or dilutable solutions, dilute emulsions, wettable powders, soluble powders, dusts, granulates, and also encapsulations in polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations of those compounds with other insecticides or acaricides and, if desired, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, e.g. especially dolomite or pulverised plant residues.

Depending on the nature of the compound of formula I to be formulated or of the combinations of those compounds with other insecticides or acaricides, suitable surface-active compounds are non-ionic, cationic and-/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, or dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl-di-(2-chloroethyl)-ethylammonium bromide.

The surfactants customarily used in the art of formulation are described, inter alia, in the following publications:

"1985 International McCutcheon's Emulsifiers & Detergents", Glen Rock N.J. USA, 1985", H. Stache, "Tensid-Taschenbuch", 2nd edition, C. Hanser Verlag Munich, Vienna 1981, M. and J. Ash "Encyclopedia of Surfactants", vol. I-III, Chemical Publishing Co., New York, 1980–1981.

The pesticidal compositions usually contain 0.1 to 99%, especially 0.1 to 95%, of a compound of formula I or combinations of that compound with other insecticides or acaricides, 1 to 99.9% of a solid or liquid adjuvant and 0 to 25%, preferably 0.1 to 20%, of a surfactant. Whereas commercial products will preferably be formulated as concentrates, the end user will normally employ dilute formulations that contain substantially lower concentrations of active ingredient. Typical concentrations are from 0.1 to 1000 ppm, preferably from 0.1 to 500 ppm. The rate of application per hectare is generally from 1 to 1000 g of active ingredient per hectare, preferably from 25 to 500 g/ha.

The preferred formulations are composed especially as follows: (throughout percentages are by weight)

Emulsifiable Concentrates

| | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |

Dusts

| | |
|---|---|
| active ingredient: | 0.1 to 10%, preferably 0.1 to 1% |
| solid carrier: | 99.9 to 90%, preferably 99.9 to 99% |

Suspension Concentrates

| | |
|---|---|
| active ingredient: | 5 to 75%, preferably 10 to 50% |
| water: | 94 to 24%, preferably 88 to 30% |
| surfactant | 1 to 40%, preferably 2 to 30% |

Wettable Powders

| | |
|---|---|
| active ingredient: | 0.5 to 90%, preferably 1 to 80% |
| surfactant: | 0.5 to 20%, preferably 1 to 15% |
| solid carrier: | 5 to 95%, preferably 15 to 90% |

Granulates

| | |
|---|---|
| active ingredient: | 0.5 to 30%, preferably 3 to 15% |
| solid carrier: | 99.5 to 70%, preferably 97 to 85% |

The compositions may also contain further auxiliaries such as stabilisers, antifoams, preservatives, viscosity regulators, binders, tackifiers as well as fertilisers or other active ingredients for obtaining special effects.

The following Examples serve to illustrate the invention but do not limit the invention.

Preparation Examples

EXAMPLE P1

1-(2,6-diisopropylphenyl)-4-isopropyl-5-thioxo-2-tetrazoline

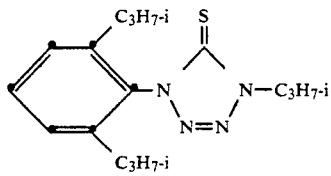

A mixture of 5.6 g of 1-(2,6-diisopropylphenyl)-4-isopropyl-5-oxo-2-tetrazoline and 5.1 g of 2,4-bis-(4-methoxyphenyl)-1,3-dithia-2,4-diphosphetane-2,4-disulfide (Lawesson's reagent) are heated at reflux for 24 hours in 60 ml of dry toluene. After evaporating off the solvent, the residue is purified by chromatography on 500 g of silica gel with hexane/ethyl acetate (19:1) as eluant. Crystallisation from hexane yields 4.2 g of 1-(2,6-diisopropylphenyl)-4-isopropyl-5-thioxo-2-tetrazoline in the form of colourless crystals, m.p. 109°–111° C.

EXAMPLE P2

1-(2,6-diisopropylphenyl)-4-isopropyl-5-oxo-2-tetrazoline

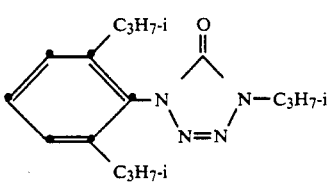

a) 1-(2,6-diisopropylphenyl)-5-oxo-2-tetrazoline 37.1 g of 2,6-diisopropylphenyl isocyanate and 50 ml of trimethylsilyl azide are stirred for 24 hours at +140° C. The mixture is then cooled to room temperature and stirred with 250 ml of toluene and with 250 ml of water. After 1 hour, the phases are separated and the aqueous phase is extracted with toluene. The combined organic phases are extracted four times with 250 ml of 15% sodium hydroxide solution each time, and then the aqueous phases are combined and washed with ether. After acidification with semi-concentrated hydrochloric acid, crude 1-(2,6-diisopropylphenyl)-5-oxo-2-tetrazoline precipitates. This is recrystallised from a mixture of hexane and toluene in a ratio of 10:1. Melting point 177°–178.5°.

b) 14.3 g of 1-(2,6-diisopropylphenyl)-5-oxo-2-tetrazoline, 12.8 g of isopropyl iodide and 10.4 g of pulverised potassium carbonate are dissolved in 140 ml of dimethylformamide and stirred for 2 hours at +60° C. The resulting suspension is poured onto water and extracted three times with ether. The combined ethereal phases are washed with water and saturated sodium chloride solution, dried over $Na_2SO_4$ and concentrated by evaporation. In order to remove the 1-(2,6-diisopropylphenyl)-5-isopropoxy-tetrazole formed as byproduct, the mixture is chromatographed on silica gel with the eluant $CH_2Cl_2$/cyclohexane (3:1). In this manner 8.7 g of 1-(2,6-diisopropylphenyl)-4-isopropyl-5-oxo-2-tetrazoline having a melting point of 60°–62° C. are obtained.

The intermediates of formulae II and VIII and compounds of formula I listed in the following Tables 1 and 2 are obtained in an analogous manner.

TABLE 1

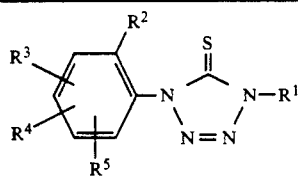

| Comp. No. | $R^1$ | $R^2$ | $R^3$ | $R^4$ | $R^5$ | physical data |
|---|---|---|---|---|---|---|
| 1.01 | $C_3H_7$-i | $C_3H_7$-i | 6-$C_3H_7$-i | H | H | m.p. 109–111° C. |
| 1.02 | $C_3H_7$-i | $C_3H_7$-i | 6-$C_2H_5$ | H | H | $n_D^{23}$ = 1.5483 |
| 1.03 | $C_3H_7$-i | $C_3H_7$-i | 6-$C_3H_7$-i | H | 4-O—$C_6H_5$ | m.p. 110.5–112° C. |
| 1.04 | $CH_3$ | $C_3H_7$-i | 6-$C_2H_5$ | H | H | m.p. 63.5–65.5° C. |
| 1.05 | $CH_2$—$C(CH_3)_3$ | $C_3H_7$-i | 6-$C_3H_7$-i | H | 4-O—$C_6H_5$ | m.p. 136–138° C. |
| 1.06 | $C_3H_7$-i | $C_5H_9$-cycl. | 6-$C_3H_7$-i | H | H | m.p. 77.5–78° C. |

TABLE 1-continued

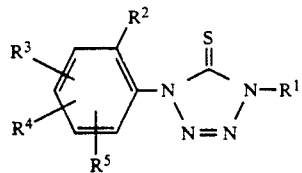

| Comp. No. | R¹ | R² | R³ | R⁴ | R⁵ | physical data |
|---|---|---|---|---|---|---|
| 1.07 | C₄H₉-s | C₅H₉-cycl. | 6-C₃H₇-i | H | H | m.p. 69.5-71.5° C. |
| 1.08 | C₂H₅ | C₃H₇-i | 6-C₃H₇-i | H | 4-O—C₆H₅ | m.p. 67.5-69° C. |
| 1.09 | CH(CH₃)COOCH₃ | C₃H₇-i | 6-C₃H₇-i | H | H | m.p. 51-54° C. |
| 1.10 | C₃H₇-i | CH₃ | 6-C₃H₇-i | H | H | $n_D^{22} = 1.5505$ |
| 1.11 | C₃H₇-i | C₂H₅ | H | H | H | $n_D^{24.5} = 1.5668$ |
| 1.12 | CH₂C(CH₃)₃ | CH₃ | 6-C₃H₇-i | H | H | m.p. 85.5-87° C. |
| 1.13 | C₅H₉-cycl. | C₃H₇-i | 6-C₃H₇-i | H | 4-O—C₆H₅ | m.p. 97-98.5° C. |
| 1.14 | C₃H₇-i | C₂H₅ | 6-C₂H₅ | H | H | $n_D^{24} = 1.5536$ |
| 1.15 | CH₂C(CH₃)₃ | C₃H₇-i | 6-C₂H₅ | H | H | $n_D^{23} = 1.5418$ |
| 1.16 | C₄H₉-s | C₃H₇-i | 6-C₂H₅ | H | H | |
| 1.17 | C₅H₉-cycl. | C₃H₇-i | 6-C₂H₅ | H | H | |
| 1.18 | CH₂C(CH₃)₃ | C₃H₇-i | 6-C₃H₇-i | H | H | m.p. 58-60° C. |
| 1.19 | C₄H₉-s | C₃H₇-i | 6-C₃H₇-i | H | H | |
| 1.20 | C₄H₉-t | C₃H₇-i | 6-C₃H₇-i | H | H | |
| 1.21 | C₅H₉-cycl. | C₃H₇-i | 6-C₃H₇-i | H | H | |
| 1.22 | CH₂—C₃H₅-cycl. | C₃H₇-i | 6-C₃H₇-i | H | H | |
| 1.23 | C(CH₃)₂—C₂H₅ | C₃H₇-i | 6-C₃H₇-i | H | H | |
| 1.24 | CH(C₂H₅)₂ | C₃H₇-i | 6-C₃H₇-i | H | H | |
| 1.25 | CH(CH₃)C₆H₁₃-n | C₃H₇-i | 6-C₃H₇-i | H | H | |
| 1.26 | C₆H₁₁-cycl. | C₃H₇-i | 6-C₃H₇-i | H | H | |
| 1.27 | (cyclohexenyl) | C₃H₇-i | 6-C₃H₇-i | H | H | m.p. 72-73° C. |
| 1.28 | CH₂C(CH₃)₃ | C₂H₅ | H | H | H | $n_D^{20.5} = 1.5560$ |
| 1.29 | C₄H₉-s | CH₃ | 6-C₃H₇-i | H | H | $n_D^{21.5} = 1.5467$ |
| 1.30 | CH₂—C₃H₅-cycl. | C₃H₇-i | 6-C₃H₇-i | H | 4-O—C₆H₅ | m.p. 95.5-97° C. |
| 1.31 | C₄H₉-s | C₃H₇-i | 6-C₃H₇-i | H | 4-CH₂C₆H₅ | m.p. 100-102° C. |
| 1.32 | CH₂C(CH₃)₃ | C₃H₇-i | 6-C₃H₇-i | H | 4-CH₂C₆H₅ | m.p. 145-146.5° C. |
| 1.33 | C₄H₉-i | C₃H₇-i | 6-C₃H₇-i | H | 4-CH₂C₆H₅ | m.p. 94-96° C. |
| 1.34 | CH₂—C₆H₅ | C₃H₇-i | 6-C₃H₇-i | H | H | |
| 1.35 | CH(CH₃)—C₆H₅ | C₃H₇-i | 6-C₃H₇-i | H | H | |
| 1.36 | CH(CH₃)—CH=CH₂ | C₃H₇-i | 6-C₃H₇-i | H | H | |
| 1.37 | CH₂—CH=CH₂ | C₃H₇-i | 6-C₃H₇-i | H | H | |
| 1.38 | CH(CH₃)CH₂OCH₃ | C₃H₇-i | 6-C₃H₇-i | H | H | $n_D^{22.5} = 1.5380$ |
| 1.39 | (cyclopentenyl) | C₃H₇-i | 6-C₃H₇-i | H | H | |
| 1.40 | C₃H₇-i | C₃H₇-i | 6-C₃H₇-i | 4-CH₃ | H | |
| 1.41 | C₃H₇-i | C₃H₇-i | 6-C₃H₇-i | 4-C₃H₇-i | H | |
| 1.42 | C₄H₉-s | C₃H₇-i | 6-C₃H₇-i | 4-CH₃ | H | |
| 1.43 | C₃H₇-i | C₃H₇-i | 6-C₃H₇-i | 4-C≡CH | H | |
| 1.44 | C₃H₇-i | C₃H₇-i | 6-CH(CH₃)—OCH₃ | H | H | |
| 1.45 | C₄H₉-s | C₃H₇-i | 6-CH(CH₃)—OCH₃ | H | H | |
| 1.46 | C₃H₇-i | C₂H₅ | 6-C₄H₉-s | H | H | |
| 1.47 | C₄H₉-s | C₂H₅ | 6-C₄H₉-s | H | H | |
| 1.48 | CH₂C(CH₃)₃ | C₂H₅ | 6-C₄H₉-s | H | H | |
| 1.49 | C₄H₉-s | C₃H₇-i | 6-C₃H₇-i | H | 4-O—C₆H₅ | |
| 1.50 | C₄H₉-t | C₃H₇-i | 6-C₃H₇-i | H | 4-O—C₆H₅ | |
| 1.51 | C(CH₃)₂—C₂H₅ | C₃H₇-i | 6-C₃H₇-i | H | 4-O—C₆H₅ | |
| 1.52 | C₃H₇-i | C₅H₉-cycl. | 6-C₃H₇-i | H | 4-O—C₆H₅ | $n_D^{23} = 1.5656$ |
| 1.53 | C₄H₉-s | C₅H₉-cycl. | 6-C₃H₇-i | H | 4-O—C₆H₅ | $n_D^{25} = 1.5647$ |
| 1.54 | CH₂C(CH₃)₃ | C₅H₉-cycl. | 6-C₃H₇-i | H | 4-O—C₆H₅ | |
| 1.55 | C₆H₁₁-cycl. | C₃H₇-i | 6-C₃H₇-i | H | 4-O—C₆H₅ | |
| 1.56 | CH(CH₃)—C₆H₅ | C₃H₇-i | 6-C₃H₇-i | H | 4-O—C₆H₅ | |
| 1.57 | C₃H₇-i | C₃H₇-i | 6-C₃H₇-i | H | 4-O—C₆H₄-2'-F | m.p. 116.5-117.5° C. |
| 1.58 | C₄H₉-s | C₃H₇-i | 6-C₃H₇-i | H | 4-O—C₆H₄-2'-F | m.p. 77-79° C. |
| 1.59 | CH₂C(CH₃)₃ | C₃H₇-i | 6-C₃H₇-i | H | 4-O—C₆H₄-2'-F | m.p. 145.5-146.5° C. |
| 1.60 | C₄H₉-t | C₃H₇-i | 6-C₃H₇-i | H | 4-O—C₆H₄-2'-F | |
| 1.61 | CH(CH₃)C₆H₅ | C₃H₇-i | 6-C₃H₇-i | H | 4-O—C₆H₄-2'-F | |
| 1.62 | C₅H₉-cycl. | C₃H₇-i | 6-C₃H₇-i | H | 4-O—C₆H₄-2'-F | |
| 1.63 | C₃H₇-i | C₅H₉-cycl. | 6-C₃H₇-i | H | 4-O—C₆H₄-2'-F | m.p. 92.5-94° C. |
| 1.64 | C₄H₉-s | C₅H₉-cycl. | 6-C₃H₇-i | H | 4-O—C₆H₄-2'-F | Smp. 63-66° C. |

TABLE 1-continued

Structure: 1,2,3,4-thiatriazole-5-thione with N-aryl substituent (R², R³, R⁴, R⁵ on phenyl) and N-R¹

| Comp. No. | R¹ | R² | R³ | R⁴ | R⁵ | physical data |
|---|---|---|---|---|---|---|
| 1.65 | $CH_2C(CH_3)_3$ | $C_5H_9$-cycl. | 6-$C_3H_7$-i | H | 4-O—$C_6H_4$-2'-F | Smp. 101–103° C. |
| 1.66 | $C_4H_9$-t | $C_5H_9$-cycl. | 6-$C_3H_7$-i | H | 4-O—$C_6H_4$-2'-F | |
| 1.67 | $C_4H_{11}$-cycl. | $C_5H_9$-cycl. | 6-$C_3H_7$-i | H | 4-O—$C_6H_4$-2'-F | |
| 1.68 | $C_3H_7$-i | $C_3H_7$-i | 6-$C_3H_7$-i | H | 4-O—$C_6H_4$-3'-F | |
| 1.69 | $C_4H_9$-s | $C_3H_7$-i | 6-$C_3H_7$-i | H | 4-O—$C_6H_4$-3'-F | |
| 1.70 | $C_5H_9$-cycl. | $C_3H_7$-i | 6-$C_3H_7$-i | H | 4-O—$C_6H_4$-3'-F | |
| 1.71 | $CH_2C(CH_3)_3$ | $C_3H_7$-i | 6-$C_3H_7$-i | H | 4-O—$C_6H_4$-3'-F | |
| 1.72 | $C_3H_7$-i | $C_3H_7$-i | 6-$C_3H_7$-i | H | 4-O—$C_6H_4$-4'-F | |
| 1.73 | $C_4H_9$-s | $C_3H_7$-i | 6-$C_3H_7$-i | H | 4-O—$C_6H_4$-4'-F | |
| 1.74 | $CH_2C(CH_3)_3$ | $C_3H_7$-i | 6-$C_3H_7$-i | H | 4-O—$C_6H_4$-4'-F | |
| 1.75 | $C_5H_9$-cycl. | $C_3H_7$-i | 6-$C_3H_7$-i | H | 4-O—$C_6H_4$-4'-F | |
| 1.76 | $C_3H_7$-i | $C_3H_7$-i | 6-$C_3H_7$-i | 4-$SCH_3$ | H | |
| 1.77 | $CH_2C(CH_3)_3$ | $C_3H_7$-i | 6-$C_3H_7$-i | 4-$SCH_3$ | H | |
| 1.78 | $C_4H_9$-s | $C_3H_7$-i | 6-$C_3H_7$-i | 4-$SCH_3$ | H | |
| 1.79 | $C_3H_7$-i | $C_3H_7$-i | 6-$C_3H_7$-i | 4-Br | H | |
| 1.80 | $C_3H_7$-i | $C_3H_7$-i | 6-$C_3H_7$-i | 4-CN | H | |
| 1.81 | $C_4H_9$-t | $C_3H_7$-i | 6-$C_3H_7$-i | H | 4-$CH_2C_6H_5$ | |
| 1.82 | $C(-CH_3)=C_2H_5$ | $C_3H_7$-i | 6-$C_3H_7$-i | H | 4-$CH_2C_6H_5$ | |
| 1.83 | $CH(CH_3)C_6H_5$ | $C_3H_7$-i | 6-$C_3H_7$-i | H | 4-$CH_2C_6H_5$ | |
| 1.84 | $C_5H_9$-cycl. | $C_3H_7$-i | 6-$C_3H_7$-i | H | 4-$CH_2C_6H_5$ | |
| 1.85 | $C_6H_{11}$-cycl. | $C_3H_7$-i | 6-$C_3H_7$-i | H | 4-$CH_2C_6H_5$ | |
| 1.86 | $C_3H_7$-i | $C_3H_7$-i | 6-$C_3H_7$-i | H | 4-$CH(CH_3)C_6H_5$ | |
| 1.87 | $C_4H_9$-s | $C_3H_7$-i | 6-$C_3H_7$-i | H | 4-$CH(CH_3)C_6H_5$ | |
| 1.88 | $CH_2C(CH_3)_3$ | $C_3H_7$-i | 6-$C_3H_7$-i | H | 4-$CH(CH_3)C_6H_5$ | |
| 1.89 | $C_3H_7$-i | $C_3H_7$-i | 6-$C_3H_7$-i | H | 4-$C_6H_5$ | |
| 1.90 | $C_4H_9$-s | $C_3H_7$-i | 6-$C_3H_7$-i | H | 4-$C_6H_5$ | |
| 1.91 | $C_3H_7$-i | $CH_3$ | 6-$CH_3$ | H | 4-O-(3,5-dichloropyridin-4-yl) | |
| 1.92 | $C_4H_9$-s | $CH_3$ | 6-$CH_3$ | H | 4-O-(3,5-dichloropyridin-4-yl) | |
| 1.93 | $C_5H_9$-cycl. | $CH_3$ | 6-$CH_3$ | H | 4-O-(3,5-dichloropyridin-4-yl) | |
| 1.94 | $C_3H_7$-i | $C_3H_7$-i | 6-$C_3H_7$-i | H | 4-S—$C_6H_5$ | |
| 1.95 | $C_4H_9$-i | $C_3H_7$-i | 6-$C_3H_7$-i | H | 4-S—$C_6H_5$ | |
| 1.96 | $C_3H_7$-i | $C_3H_7$-i | 6-$C_3H_7$-i | H | 4-N(CHO)—$C_6H_5$ | |
| 1.97 | $C_4H_9$-s | $C_3H_7$-i | 6-$C_3H_7$-i | H | 4-N(CHO)—$C_6H_5$ | |
| 1.98 | $CH_2C(CH_3)_3$ | $C_3H_7$-i | 6-$C_3H_7$-i | H | 4-N(CHO)—$C_6H_5$ | |
| 1.99 | $C_5H_9$-cycl. | $C_3H_7$-i | 6-$C_3H_7$-i | H | 4-N(CHO)—$C_6H_5$ | |
| 1.100 | $C_6H_{11}$-cycl. | $C_3H_7$-i | 6-$C_3H_7$-i | H | 4-N(CHO)—$C_6H_5$ | |
| 1.101 | $C_4H_9$-t | $C_3H_7$-i | 6-$C_3H_7$-i | H | 4-N(CHO)—$C_6H_5$ | |
| 1.102 | $C_3H_7$-i | $C_3H_7$-i | 6-$C_3H_7$-i | H | 4-N(CHO)—$C_6H_4$-2'-F | |
| 1.103 | $C_4H_9$-s | $C_3H_7$-i | 6-$C_3H_7$-i | H | 4-N(CHO)—$C_6H_4$-2'-F | |
| 1.104 | $CH_2C(CH_3)_3$ | $C_3H_7$-i | 6-$C_3H_7$-i | H | 4-N(CHO)—$C_6H_4$-2'-F | |
| 1.105 | $C_3H_7$-i | $C_4H_9$-t | 6-$CH_3$ | H | H | m.p. 89.5–91° C. |
| 1.106 | $C_4H_9$-s | $C_4H_9$-t | 6-$CH_3$ | H | H | m.p. 76–77° C. |
| 1.107 | $CH_2C(CH_3)_3$ | $C_4H_9$-t | 6-$CH_3$ | H | H | m.p. 116–119° C. |
| 1.108 | $C(CH_3)_2$—C≡CH | $C_3H_7$-i | 6-$C_2H_5$ | H | H | |
| 1.109 | $C(CH_3)_2$—C≡CH | $C_3H_7$-i | 6-$C_3H_7$-i | H | H | |
| 1.110 | $C(CH_3)_2$—C≡CH | $C_3H_7$-i | 6-$C_3H_7$-i | H | 4-O—$C_6H_5$ | |
| 1.111 | $C(CH_3)_2$—C≡CH | $C_3H_7$-i | 6-$C_3H_7$-i | H | 4-O—$C_6H_4$-2'-F | |
| 1.112 | $C(CH_3)_2$—CH=CH | $C_3H_7$-i | 6-$C_3H_7$-i | H | H | |
| 1.113 | $C(CH_3)_2$—CH=CH | $C_3H_7$-i | 6-$C_3H_7$-i | H | 4-O—$C_6H_5$ | |
| 1.114 | $C(CH_3)_3$—C≡CH | $C_2H_5$ | 6-$C_4H_9$-s | H | H | |

TABLE 1-continued

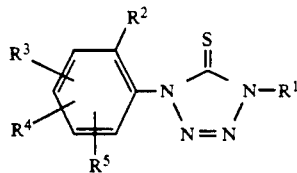

| Comp. No. | R¹ | R² | R³ | R⁴ | R⁵ | physical data |
|---|---|---|---|---|---|---|
| 1.115 | C(CH$_3$)$_3$—C≡CH | C$_2$H$_5$ | 6-C$_4$H$_9$-s | H | 4-O—C$_6$H$_5$ | |
| 1.116 | CH$_3$ | C$_3$H$_7$-i | 6-C$_3$H$_7$-i | H | 4-O—C$_6$H$_5$ | m.p. 80-83.5° C. |
| 1.117 | C$_4$H$_9$-s | C$_2$H$_5$ | 6-C$_2$H$_5$ | H | H | m.p. 50-52° C. |
| 1.118 | C$_3$H$_7$-i | CH$_3$ | 6-CH$_3$ | H | H | m.p. 101-103° C. |
| 1.119 | C$_4$H$_2$-s | CH$_3$ | 6-CH$_3$ | H | H | m.p. 44-46° C. |
| 1.120 | C$_4$H$_9$-s | C$_2$H$_5$ | H | H | H | $n_D^{23}$ = 1.5607 |
| 1.121 | C$_4$H$_9$-t | C$_5$H$_9$-cycl. | 6-C$_3$H$_7$-i | H | 4-O—C$_6$H$_5$ | m.p. 101-103° C. |
| 1.122 | C$_3$H$_7$-i | C$_4$H$_9$-s | 6-C$_4$H$_9$-s | H | 4-C$_6$H$_5$ | m.p. 119-121° C. |
| 1.123 | —CH(CH$_3$)—CH$_2$—OCH$_3$ | C$_3$H$_7$-i | 6-C$_3$H$_7$-i | H | 4-O—C$_6$H$_5$ | m.p. 93.5-94.5° C. |
| 1.124 | C$_3$H$_7$-i | C$_3$H$_7$-i | H | H | H | |
| 1.125 | C$_4$H$_9$-s | C$_3$H$_7$-i | H | H | H | |
| 1.126 | C$_4$H$_9$-s | C$_3$H$_7$-i | 6-C$_3$H$_7$-i | H | 4-O—C$_6$H$_4$-2'-Cl | |
| 1.127 | C$_3$H$_7$-i | C$_3$H$_7$-i | 6-C$_3$H$_7$-i | H | 4-O—C$_6$H$_4$-2'-Cl | |

TABLE 2

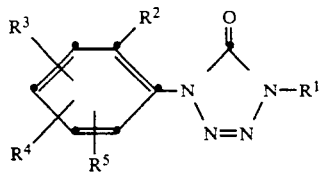

| Comp. No. | R¹ | R² | R³ | R⁴ | R⁵ | physical data |
|---|---|---|---|---|---|---|
| 2.01 | C$_3$H$_7$-i | C$_3$H$_7$-i | 6-C$_3$H$_7$-i | H | H | m.p. 60-62° C. |
| 2.02 | C$_3$H$_7$-i | C$_3$H$_7$-i | 6-C$_2$H$_5$ | H | H | $n_D^{23}$ = 1.5141 |
| 2.03 | C$_3$H$_7$-i | C$_3$H$_7$-i | 6-C$_3$H$_7$-i | H | 4-O—C$_6$H$_5$ | $n_D^{21.5}$ = 1.5429 |
| 2.04 | CH$_3$ | C$_3$H$_7$-i | 6-C$_2$H$_5$ | H | H | m.p. 52.5-55 |
| 2.05 | CH$_2$C(CH$_3$)$_3$ | C$_3$H$_7$-i | 6-C$_3$H$_7$-i | H | 4-O—C$_6$H$_5$ | * |
| 2.06 | C$_3$H$_7$-i | C$_5$H$_9$-cycl. | 6-C$_3$H$_7$-i | H | H | $n_D^{24}$ = 1.5262 |
| 2.07 | C$_3$H$_7$-s | C$_5$H$_9$-cycl. | 6-C$_3$H$_7$-i | H | H | $n_D^{24}$ = 1.5236 |
| 2.08 | C$_2$H$_5$ | C$_3$H$_7$-i | 6-C$_3$H$_7$-i | H | 4-O—C$_6$H$_5$ | m.p. 80-81° C. |
| 2.09 | CH(CH$_3$)COOCH$_3$ | C$_3$H$_7$-i | 6-C$_3$H$_7$-i | H | H | m.p. 58-60° C. |
| 2.10 | C$_3$H$_7$-i | C$_3$H$_7$-i | CH$_3$ | H | H | $n_D^{24}$ = 1.5147 |
| 2.11 | C$_3$H$_7$-i | C$_2$H$_5$ | H | H | H | $n_D^{22}$ = 1.5260 |
| 2.12 | CH$_2$C(CH$_3$)$_3$ | CH$_3$ | 6-C$_3$H$_7$-i | H | H | * |
| 2.13 | C$_5$H$_9$-cycl. | C$_3$H$_7$-i | 6-C$_3$H$_7$-i | H | 4-O—C$_6$H$_5$ | $n_D^{23.5}$ = 1.5493 |
| 2.14 | CH$_2$C(CH$_3$)$_3$ | C$_3$H$_7$-i | 6-C$_2$H$_5$ | H | H | * |
| 2.15 | CH$_2$C(CH$_3$)$_3$ | C$_3$H$_7$-i | 6-C$_3$H$_7$-i | H | H | * |
| 2.16 | CH$_2$C(CH$_3$)$_3$ | C$_2$H$_5$ | H | H | H | * |
| 2.17 | C$_4$H$_9$-s | CH$_3$ | 6-C$_3$H$_7$-i | H | H | * |
| 2.18 | CH$_2$—C$_3$H$_5$cycl. | C$_3$H$_7$-i | 6-C$_3$H$_7$-i | H | 4-O—C$_6$H$_5$ | m.p. 118.5-120° C. |
| 2.19 | C$_4$H$_9$-s | C$_3$H$_7$-i | 6-C$_3$H$_7$-i | H | 4-CH$_2$C$_6$H$_5$ | m.p. 71-73° C. |
| 2.20 | CH$_2$C(CH$_3$)$_3$ | C$_3$H$_7$-i | 6-C$_3$H$_7$-i | H | 4-CH$_2$C$_6$H$_5$ | * |
| 2.21 | C$_3$H$_7$-i | C$_3$H$_7$-i | 6-C$_3$H$_7$-i | H | 4-CH$_2$C$_6$H$_5$ | * |
| 2.22 | CH$_3$ | C$_3$H$_7$-i | 6-C$_3$H$_7$-i | H | 4-O—C$_6$H$_5$ | m.p. 107-108° C. |
| 2.23 | H | C$_3$H$_7$-i | 6-C$_3$H$_7$-i | H | H | m.p. 177-178.5° C. |
| 2.24 | H | C$_3$H$_7$-i | 6-C$_2$H$_5$ | H | H | m.p. 124-125° C. |
| 2.25 | H | C$_3$H$_7$-i | 6-C$_3$H$_7$-i | H | 4-OC$_6$H$_5$ | m.p. 221-224° C. |
| 2.26 | H | C$_5$H$_9$-cycl. | 6-C$_3$H$_7$-i | H | H | m.p. 166-167.5° C. |
| 2.27 | H | CH$_3$ | 6-C$_3$H$_7$-i | H | H | m.p. 147.5-148.5° C. |
| 2.28 | H | C$_2$H$_5$ | H | H | H | m.p. 117-118.5° C. |
| 2.29 | H | C$_3$H$_7$-i | 6-C$_3$H$_7$-i | H | 4-CH$_2$C$_6$H$_5$ | m.p. 199-201° C. |
| 2.30 | H | C$_3$H$_7$-i | 6-C$_3$H$_7$-i | H | 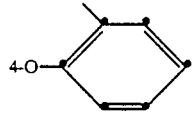 | m.p. 218-220° C. |

TABLE 2-continued

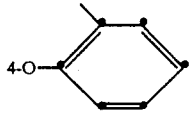

| Comp. No. | R¹ | R² | R³ | R⁴ | R⁵ | physical data |
|---|---|---|---|---|---|---|
| 2.31 | $CH_2C(CH_3)_3$ | $C_3H_7$-i | 6-$C_3H_7$-i | H | 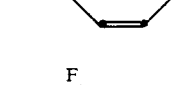 | * |
| 2.32 | $C_3H_7$-i | $C_2H_5$ | 6-$C_2H_5$ | H | H | * |
| 2.33 | H | $C_2H_5$ | 6-$C_2H_5$ | H | H | m.p. 92–94° C. |
| 2.34 | $C_4H_9$-s | $C_2H_5$ | 6-$C_2H_5$ | H | H | * |
| 2.35 | $C_3H_7$-i | $CH_3$ | 6-$CH_3$ | H | H | * |
| 2.36 | H | $CH_3$ | 6-$CH_3$ | H | H | m.p. 142–144° C. |
| 2.37 | $C_4H_9$-s | $CH_3$ | 6-$CH_3$ | H | H | * |
| 2.38 | $CH_2C(CH_3)_3$ | $CH_3$ | 6-$C_4H_9$-t | H | H | * |
| 2.39 | H | $CH_3$ | 6-$C_4H_9$-t | H | H | m.p. 198–199.5° C. |
| 2.40 | $C_4H_9$-s | $C_2H_5$ | H | H | H | * |
| 2.41 | $CH_2C(CH_3)_3$ | $C_5H_9$-cycl. | 6-$C_3H_7$-i | H | 4-$OC_6H_5$ | * |
| 2.42 | H | $C_5H_9$-cycl. | 6-$C_3H_7$-i | H | 4-$OC_6H_5$ | m.p. 214.5–216° C. |
| 2.43 | $C_3H_7$-i | $C_3H_7$-i | 6-$C_3H_7$-i | H | 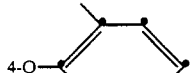 | m.p. 101–102° C. |
| 2.44 | $C_4H_9$-s | $C_3H_7$-i | 6-$C_3H_7$-i | H | 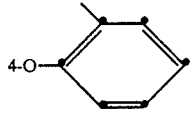 | m.p. 66–68° C. |
| 2.45 | $C_3H_7$-i | $CH_3$ | 6-$C_3H_9$-t | H | H | $n_D^{25}$ = 1.5179 |
| 2.46 | $C_3H_7$-i | $C_4H_9$-s | 6-$C_4H_9$-s | H | 4-$C_6H_5$ | * |
| 2.47 | H | $C_4H_9$-s | 6-$C_4H_9$-s | H | 4-$C_6H_5$ | m.p. 170–172° C. |
| 2.48 | $C_4H_9$-s | $CH_3$ | 6-$C_4H_9$-t | H | H | $n_D^{20}$ = 1.5180 |
| 2.49 | $C_3H_7$-i | $C_5H_9$-cycl. | 6-$C_3H_7$-i | H | 4-$OC_6H_5$ | $n_D^{22}$ = 1.5450 |
| 2.50 | $C_4H_9$-s | $C_5H_9$-cycl. | 6-$C_3H_7$-i | H | 4-$OC_6H_5$ | $n_D^{21}$ = 1.5465 |
| 2.51 | $CH(CH_3)CH_2OCH_3$ | $C_3H_7$-i | 6-$C_3H_7$-i | H | H | * |
| 2.52 | $CH(CH_3)CH_2OCH_3$ | $C_3H_7$-i | 6-$C_3H_7$-i | H | 4-$OC_6H_5$ | * |
| 2.53 | $CH_2C(CH_3)_3$ | $C_5H_9$-cycl. | 6-$C_3H_7$-i | H | 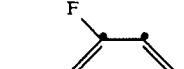 | * |
| 2.54 | H | $C_5H_9$-cycl. | 6-$C_3H_7$-i | H | 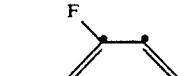 | m.p. 212–213.5° C. |
| 2.55 | $C_4H_9$-s | $C_5H_9$-cycl. | 6-$C_3H_7$-i | H |  | $n_D^{20}$ = 1.5398 |

TABLE 2-continued

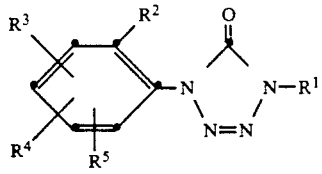

| Comp. No. | R¹ | R² | R³ | R⁴ | R⁵ | physical data |
|---|---|---|---|---|---|---|
| 2.56 | $C_3H_7$-i | $C_5H_9$-cycl. | 6-$C_3H_7$-i | H | 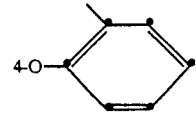 4-O— with 2-F | $n_D^{20} = 1.5435$ |
| 2.57 | $C_3H_7$-i | $C_3H_7$-i | H | H | H | |
| 2.58 | $C_4H_9$-s | $C_3H_7$-i | H | H | H | |
| 2.59 | H | $C_3H_7$-i | H | H | H | |
| 2.60 | $C_3H_7$-i | $C_2H_5$ | 6-$C_4H_9$-s | H | H | |
| 2.61 | $C_4H_9$-s | $C_2H_5$ | 6-$C_4H_9$-s | H | H | |
| 2.62 | $CH_2C(CH_3)_3$ | $C_2H_5$ | 6-$C_4H_9$-s | H | H | |
| 2.63 | H | $C_2H_5$ | 6-$C_4H_9$-s | H | H | |
| 2.64 | $C_3H_7$-i | $C_3H_7$-i | 6-$C_3H_7$-i | H | 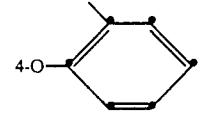 4-O— with 2-Cl | |
| 2.65 | $C_4H_9$-s | $C_3H_7$-i | 6-$C_3H_7$-i | H | 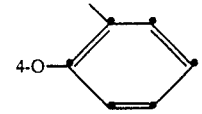 4-O— with 2-Cl | |
| 2.66 | H | $C_3H_7$-i | 6-$C_3H_7$-i | H | 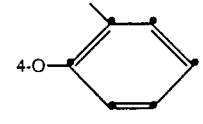 4-O— with 2-Cl | |
| 2.67 | $C_3H_7$-i | $C_3H_7$-i | 6-$C_3H_7$-i | H | 4-$CH(CH_3)C_6H_5$ | m.p. 67.5–69.5° C. |
| 2.68 | $C_4H_9$-s | $C_3H_7$-i | 6-$C_3H_7$-i | H | 4-$CH(CH_3)C_6H_5$ | $n_D^{21} = 1.5365$ |
| 2.69 | H | $C_3H_7$-i | 6-$C_3H_7$-i | H | 4-$CH(CH_3)C_6H_5$ | m.p. 191.5–193.5° C. |
| 2.70 | $C_3H_7$-i | $CH_3$ | 6-$CH_3$ | H | 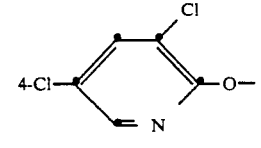 4-Cl, pyridyl-O— with Cl | * |
| 2.71 | $C_4H_9$-s | $CH_3$ | 6-$CH_3$ | H | 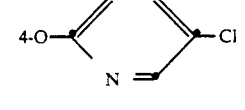 4-O-pyridyl with Cl substituents | * |

TABLE 2-continued

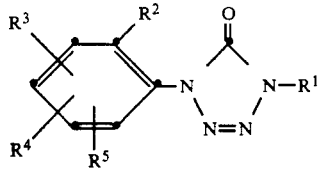

| Comp. No. | R¹ | R² | R³ | R⁴ | R⁵ | physical data |
|---|---|---|---|---|---|---|
| 2.72 | H | CH₃ | 6-CH₃ | H | 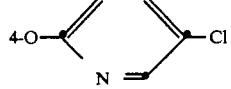 | m.p. 175.5–179° C. |

*yellow oils that can be used in the thionation reaction without being further purified. These oils contain, in addition to the product indicated, the isomeric 1-phenyl-5-alkoxy-tetrazole of formula

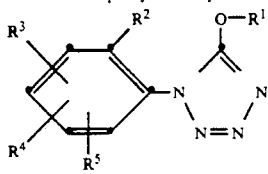

FORMULATION EXAMPLES (throughout, percentages are by weight)

EXAMPLE F1

Emulsifiable Concentrates

|  | a) | b) |
|---|---|---|
| compound No. 1.03 | 10% | 25% |
| calcium dodecylbenzenesulfonate | — | 5% |
| castor oil polyethylene glycol ether (36 moles of ethylene oxide) | 25% | 5% |
| cyclohexanone | — | 40% |
| butanol | 15% | — |
| xylene mixture | — | 25% |
| ethyl acetate | 50% | — |

Emulsions of any desired concentration can be produced from such concentrates by dilution with water.

EXAMPLE F2

Solutions

|  | a) | b) |
|---|---|---|
| compound No. 1.01 10% 5% | 70% | — |
| polyethylene glycol (mol. wt. 400) |  |  |
| N-methyl-2-pyrrolidone | 20% | 20% |
| epoxidised coconut oil | — | 1% |
| petroleum fraction (boiling range 160–190° C.) | — | 74% |

These solutions are suitable for application in the form of micro-drops.

EXAMPLE F3

Granulates

|  | a) | b) |
|---|---|---|
| compound No. 1.02 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

EXAMPLE F4

Extruder Granulate

| compound No. 1.05 | 10% |
|---|---|
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

EXAMPLE F5

Coated Granulate

| compound No. 1.04 | 3% |
|---|---|
| polyethylene glycol (mol. wt. 400) | 3% |
| kaolin | 94% |

The finely ground active ingredient is uniformly applied, in a mixer, to the kaolin moistened with polyethylene glycol. Non-dusty coated granulates are obtained in this manner.

EXAMPLE F6

Dusts

|  | a) | b) | c) | d) |
|---|---|---|---|---|
| compound No. 1.03 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by homogeneously mixing the carriers with the active ingredient and where appropriate grinding in a suitable mill.

EXAMPLE F7

Wettable Powders

|  | a) | b) | c) |
|---|---|---|---|
| compound No. 1.06 | 20% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is ground in a suitable mill, affording wettable powders which can be diluted with water to give suspensions of the desired concentration.

EXAMPLE F8

Suspension Concentrate

| compound No. 1.13 | 40% |
|---|---|
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is homogeneously mixed with the adjuvants, giving a suspension concentrate from which suspensions of any desired concentration can be obtained by dilution with water.

BIOLOGICAL EXAMPLES

EXAMPLE B1

Action against *Diabrotica balteata* larvae

Maize seedlings are sprayed with an aqueous emulsion spray formulation containing 400 ppm of the active ingredient. When the spray coating has dried, the maize seedlings are each populated with 10 larvae of *Diabrotica balteata* in the $L_2$ stage and placed in a plastics container. Evaluation is carried out six days later. The percentage reduction in population (% effect) is ascertained by comparing the number of dead larvae on the treated plants with the number of dead larvae on the untreated plants.

Compounds from Table 1 exhibit a good activity against *Diabrotica balteata* in this test. Compounds 1.01, 1.02, 1.03, 1.05, 1.10, 1.12, 1.33, 1.30, 1.18, 1.31, 1.59, 1.14, 1.107, 1.57, 1.58, 1.105, 1.106 and 1.52 are more than 80% effective.

EXAMPLE B2

Action against *Tetranychus urticae*

Young bean plants are populated with a mixed population of *Tetranychus urticae* and sprayed 1 day later with an aqueous emulsion spray formulation containing 400 ppm of the active ingredient. The plants are then incubated for 6 days at 25° C. and subsequently evaluated. The percentage reduction in population (% effect) is ascertained by comparing the number of dead eggs, larvae and adults on the treated plants with that on the untreated plants.

Compounds from Table 1 exhibit a good activity against *Tetranychus urticae* in this test. Compounds 1.03, 1.05, 1.07, 1.13, 1.33, 1.30, 1.31, 1.29, 1.57, 1.105 and 1.52 reduce the population by more than 80%.

EXAMPLE B3

Action against *Spodoptera littoralis* caterpillars

Young soybean plants are sprayed with an aqueous emulsion spray formulation containing 400 ppm of the active ingredient. When the spray coating has dried the soybean plants are each populated with 10 caterpillars of *Spodoptera littoralis* in the $L_3$ stage and placed in a plastics container. The evaluation is carried out 3 days later. The percentage reduction in population and the percentage reduction in feeding damage (% effect) are ascertained by comparing the number of dead caterpillars and the feeding damage, respectively, on the treated and untreated plants.

Compounds from Table 1 exhibit a good activity against *Spodoptera littoralis* in this test. Compound 1.03 causes a reduction in population of more than 80% even at 50 ppm.

EXAMPLE B4

Action against *Crocidolomia binotalis* caterpillars

Young cabbage plants are sprayed with an aqueous emulsion spray formulation containing 400 ppm of the active ingredient. When the spray coating has dried the cabbage plants are each populated with 10 caterpillars of *Crocidolomia binotalis* in the $L_3$ stage and placed in a plastics container. The evaluation is carried out 3 days later. The percentage reduction in population and the percentage reduction in feeding damage (% effect) are ascertained by comparing the number of dead caterpillars and the feeding damage, respectively, on the treated and untreated plants.

Compounds from Table 1 exhibit a good activity against *Crocidolomia binotalis* in this test. Compound 1.03 is more than 80% effective even at 50 ppm.

EXAMPLE B5

Action against *Anthonomus grandis* adults

Young cotton plants are sprayed with an aqueous emulsion spray formulation containing 400 ppm of the active ingredient. When the spray coating has dried the cotton plants are each populated with 10 *Anthonomus grandis* adults and placed in a plastics container. The evaluation is carried out 3 days later. The percentage reduction in population and the percentage reduction in feeding damage (% effect) are ascertained by comparing the number of dead beetles and the feeding damage, respectively, on the treated and untreated plants.

Compounds from Table 1 exhibit a good activity against *Anthonomus grandis* in this test. Compound 1.03 is still more than 80% effective even at 200 ppm.

EXAMPLE B6

Systemic action against *Nilaparvata lugens*

Approximately 10-day-old rice plants are each placed in a plastics beaker which contains 20 ml of an aqueous emulsion formulation of the test compound in a concentration of 50 ppm and which is closed with a perforated plastics lid. The root of each rice plant is pushed through a hole in the plastics lid into the aqueous test formulation. The rice plant is then populated with 20 nymphs of *Nilaparvata lugens* in the N₂ to N₃ stage and covered with a plastics cylinder. The test is carried out at 26° C. and approximately 60% relative humidity with a period of exposure to light of 16 hours. After two and five days the number of dead test insects is ascertained in comparison with untreated controls.

Compounds from Table 1 exhibit a good activity against *Nilaparvata lugens* in the above test. Compounds 1.01, 1.02, 1.03, 1.04, 1.06, 1.07, 1.10, 1.12, 1.18, 1.29, 1.14, 1.107, 1.105 and 1.106 are 80–100% effective.

EXAMPLE B7

Action against *Nilaparvata lugens*

Rice plants are treated with an aqueous emulsion spray formulation containing 400 ppm of the active ingredient. When the spray coating has dried, the rice plants are each populated with cicada larvae in the L₂ and L₃ stage. The evaluation is carried out 21 days later. The percentage reduction in population (% effect) is ascertained by comparing the number of surviving cicadas on the treated plants with the number on the untreated plants.

Compounds from Table 1 exhibit a good activity against *Nilaparvata lugens* in this test. In particular, compounds 1.01, 1.02, 1.03, 1.06, 1.05 , 1.08, 1.07, 1.13, 1.12, 1.33, 1.30, 1.18, 1.32, 1.29, 1.27, 1.14, 1.107, 1.57, 1.58, 1.105 and 1.106 are more than 80% effective.

EXAMPLE B8

Action against *Nephotettix cincticeps*

Rice plants are treated with an aqueous emulsion spray formulation containing 400 ppm of the active ingredient. When the spray coating has dried, the rice plants are each populated with cicada larvae in the L₂ and L₃ stage. The evaluation is carried out 21 days later. The percentage reduction in population (% effect) is ascertained by comparing the number of surviving cicadas on the treated plants with the number on untreated plants.

Compounds from Table 1 exhibit a good activity against *Nephotettix cincticeps* in this test. In particular, compounds 1.01, 1.03, 1.05, 1.08, 1.33, 1.107, 1.57, 1.58, 1.105 and 1.106 are 80–100% effective.

EXAMPLE B9

Action against *Aphis craccivora*

Pea seedlings are infested with *Aphis craccivora* and then sprayed with a spray formulation containing 400 ppm of the test compound and incubated at 20° C. The evaluation is carried out 3 and 6 days later. The percentage reduction in population (% effect) is ascertained by comparing the number of dead aphids on the treated plants with the number on the untreated plants.

Compounds from Table 1 exhibit a good activity against *Aphis craccivora* in this test. In particular, compounds 1.01, 1.02, 1.07, 1.11 and 1.14 are more than 80% effective.

EXAMPLE B10

Action against *Boophilus microplus*

Fully replete adult female ticks are affixed to a PVC plate and covered with a cottonwool swab. For the treatment, 10 ml of an aqueous test solution containing 125 ppm of the test compound are poured over the test organisms. The cottonwool swab is then removed and the ticks are incubated for 4 weeks for oviposition. The activity against *Boophilus microplus* is demonstrated by death or sterility of the females or, in the case of eggs, by ovicidal action.

The compounds according to Table 1 exhibit a good activity against *Boophilus microplus* in this test. In particular, compounds 1.01, 1.02, 1.03, 1.05, 1.08, 1.13, 1.18, 1.30, 1.38, 1.33 and 1.59 are more than 80% effective.

EXAMPLE B11

Action against *Musca domestica*

A sugar cube is so treated with a solution of the test substance that the concentration of test substance in the sugar after drying overnight is 250 ppm. This treated cube is placed with a wet cottonwool swab and 10 adult (approximately 1-week-old) flies [species *M. domestica*; Schmidlin strain (organophosphate-resistant)] on an aluminium dish. The whole is covered with a beaker glass and left for 24 hours at 25° C. and 50% humidity. The mortality rate is determined at the end of this period.

The compounds of Table 1 exhibit a good activity against *Musca domestica* in this test. In particular, compounds 1.08, 1.30 and 1.58 are more than 80% effective.

EXAMPLE B12

Action against *Heliothis virescens* caterpillars

Young soybean plants are sprayed with an aqueous emulsion spray formulation containing 400 ppm of the active ingredient. When the spray coating has dried, the soybean plants are each populated with 10 caterpillars of *Heliothis virescens* in the first stage and placed in a plastics container. The evaluation is carried out 6 days later. The percentage reduction in population and the percentage reduction in feeding damage (% effect) is ascertained by comparing the number of dead caterpillars and the feeding damage, respectively, on the treated and untreated plants.

Compounds from Table 1 exhibit a good activity against *Heliothis virescens* in this test. In particular, compounds 1.33 and 1.31 are more than 80% effective.

What is claimed is:

1. A 1-phenyl-5-thioxo-2-tetrazoline of formula I

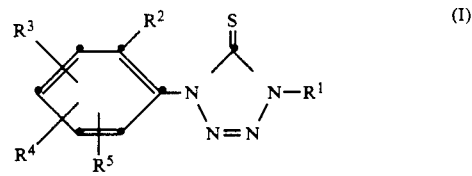

in which $R^1$ is $C_1$–$C_8$alkyl, $C_3$–$C_6$alkenyl, $C_3$–$C_6$alkynyl, $C_3$–$C_6$-cycloalkyl, $C_5$–$C_6$-cycloalkenyl, $C_1$–$C_4$alkyl- or halo-substituted $C_3$–$C_6$cycloalkyl, $C_1$–$C_4$-alkyl- or halo-substituted $C_5$–$C_6$cycloalkenyl, halo-, $C_1$–$C_4$alkoxy- or phenyl-substituted $C_3$–$C_6$alkenyl, halo-, $C_1$–$C_4$alkoxy- or phenyl-substituted $C_3$–$C_8$alkynyl, or $C_1$–$C_8$alkyl that is substituted by halogen, $C_1$–$C_4$-alkoxy, $C_1$–$C_4$alkylthio, $C_1$–$C_4$alkoxycarbonyl, $C_3$–$C_6$cycloalkyl, phenyl, cyano, hydroxy, halophenyl, $C_1$–$C_4$alkylphenyl or by a heteroaromatic radical, $R^2$ is $C_1$–$C_6$alkyl, $C_2$–$C_6$alkenyl, $C_2$–$C_6$alkynyl, $C_3$–$C_6$-cycloalkyl, cyclopentenyl or cyclohexenyl, or is $C_1$–$C_6$alkyl that is substituted by halogen, by $C_1$–$C_4$alkoxy or by $C_1$–$C_4$alkylthio, each of $R^3$ and $R^4$, independently of the other, is hydrogen, halogen, $C_1-C_4$alkyl, $C_1-C_4$haloalkyl, $C_1-C_4$alkoxy, $C_1-C_4$alkylthio, $C_3-C_6$cycloalkyl, $C_2-C_4$alkenyl, $C_2-C_4$alkynyl, $C_2-C_6$alkoxyalkyl, $C_2-C_6$alkylthioalkyl, $C_1-C_4$cyanoalkyl, phenyl-$C_2-C_4$alkenyl or phenyl-$C_2-C_4$alkynyl, or $R^3$ and $R^4$ together are a —CH=CH—CH=CH—, —CH$_2$—CH=CH—, —(CH$_2$)$_4$—, —(CH$_2$)$_3$—, —O—CH$_2$—O—, —O—CH$_2$—CH$_2$—O—, —CH$_2$—O—CH$_2$—, —(CH$_2$)$_2$—CH=CH— or —CH$_2$—CH=CH—CH$_2$— bridge, each of which may be substituted by one or two $C_1-C_4$alkyl groups, and $R^5$ is hydrogen or a —Z—$R^6$ group in which $R^6$ is phenyl, naphthyl or pyridyl, or is phenyl, napthyl or pyridyl each of which is substituted by one or two substituents selected from the group consisting of halogen, $C_1-C_4$alkyl, $C_1-C_4$alkoxy, $C_1-C_4$haloalkoxy, $C_1-C_4$haloalkyl, $C_1-C_4$alkylthio, $C_1-C_4$haloalkylthio, di-$C_1-C_4$alkylamino, nitro, cyano, $C_1-C_4$alkoxycarbonyl and $C_1-C_4$alkylcarbonyl, and Z is oxygen, sulfur, a direct bond, —NH—, —N($C_1-C_2$alkyl)—, —N(CHO)—, —CH$_2$—, —CH(CH$_3$)— or —C(CH$_3$)$_2$—.

2. A compound according to claim 1, wherein $R^1$ is $C_1-C_5$alkyl, $C_3-C_5$-alkenyl, $C_3-C_5$alkynyl, $C_5-C_6$cycloalkyl, or $C_1-C_4$alkyl that is substituted by $C_1-C_4$alkoxy, by phenyl or by cyclopropyl.

3. A compound according to claim 1, wherein $R^2$ is $C_1-C_4$alkyl or $C_5-C_6$-cycloalkyl.

4. A compound according to claim 1, wherein each of $R^3$ and $R^4$, independently of the other, is hydrogen, $C_1-C_4$alkyl, $C_2-C_3$alkynyl, $C_2-C_3$alkenyl or $C_2-C_4$alkoxyalkyl.

5. A compound according to claim 4, wherein one of the substituents $R^3$ and $R^4$ is hydrogen and the other occupies the 6-position of the phenyl ring.

6. A compound according to claim 1, wherein $R^5$ is hydrogen, benzyl, 1-phenethyl, phenoxy, halophenoxy, phenylthio, phenyl, dichloropyridyloxy, N-formylanilinyl or N-formylhaloanilinyl.

7. A compound according to claim 6, wherein $R^5$ is hydrogen, benzyl, phenoxy or halophenoxy in the 4-position of the phenyl ring.

8. A compound according to claim 5, wherein $R^3$ is $C_1-C_4$alkyl in the 6-position of the phenyl ring and $R^4$ is hydrogen.

9. A compound according to claim 1, wherein $R^2$ is $C_1-C_4$alkyl or $C_5-C_6$-cycloalkyl, $R^3$ is $C_1-C_4$alkyl in the 6-position of the phenyl ring, $R^4$ is hydrogen and $R^5$ is hydrogen, benzyl, phenoxy or halophenoxy in the 4-position of the phenyl ring.

10. A compound according to claim 1, wherein $R^1$ is $C_1-C_5$alkyl, $C_3-C_5$-alkenyl, $C_3-C_5$alkynyl, $C_5-C_6$cycloalkyl, or $C_1-C_4$alkyl that is substituted by $C_1-C_4$alkoxy, by phenyl or by cyclopropyl, $R^2$ is $C_1-C_4$alkyl or $C_5-C_6$-cycloalkyl, each of $R^3$ and $R^4$, independently of the other, is hydrogen, $C_1-C_4$alkyl, $C_2-C_3$alkynyl, $C_2-C_3$alkenyl or $C_2-C_4$alkoxyalkyl and $R^5$ is hydrogen, benzyl, 1-phenethyl, phenoxy, halophenoxy, phenylthio, phenyl, dichloropyridyloxy, N-formylanilinyl or N-formylhaloanilinyl.

11. A compound according to claim 1, wherein $R^1$ is $C_1-C_5$alkyl or $C_5-C_6$-cycloalkyl, $R^2$ is $C_1-C_4$alkyl or $C_5-C_6$cycloalkyl, $R^3$ is $C_1-C_4$alkyl in the 6-position of the phenyl ring, $R^4$ is hydrogen, and $R^5$ is hydrogen, benzyl, phenoxy or halophenoxy in the 4-position of the phenyl ring.

12. A compound according to claim 1 selected from the group selected from 1-(2-ethyl-6-isopropylphenyl)-4-isopropyl-5-thioxo-2-tetrazoline, 1-(2,6-diisopropyl-4-phenoxyphenyl)-4-isopropyl-5-thioxo-2-tetrazoline, 1-(2-ethyl-6-isopropylphenyl)-4-methyl-5-thioxo-2-tetrazoline, 1-(2,6-diisopropyl-4-phenoxyphenyl)-4-(2,2-dimethylpropyl)-5-thioxo-2-tetrazoline, 1-(2-cyclopentyl-6-isopropylphenyl)-4-isopropyl-5-thioxo-2-tetrazoline, 1-(2-cyclopentyl-6-isopropylphenyl)-4-sec.-butyl-5-thioxo-2-tetrazoline, 1-(2,6-diisopropyl-4-phenoxyphenyl)-4-ethyl-5-thioxo-2-tetrazoline, 1-(2,6-diisopropylphenyl)-4-(1-methyl-2-methoxyethyl)-5-thioxo-2-tetrazoline, 1-(2-methyl-6-isopropylphenyl)-4-isopropyl-5-thioxo-2-tetrazoline, 1-(2-methyl-6-isopropylphenyl)-4-(2,2-dimethylpropyl)-5-thioxo-2-tetrazoline, 1-(2,6-diisopropyl-4-phenoxyphenyl)-4-cyclopentyl-5-thioxo-2-tetrazoline, 1-(2,6-diisopropylphenyl)-4-isopropyl-5-thioxo-2-tetrazoline, 1-(2-ethyl-6-isopropylphenyl)-4-(2,2-dimethylpropyl)-5-thioxo-2-tetrazoline, 1-(2,6-diisopropylphenyl)-4-(2,2-dimethylpropyl)-5-thioxo-2-tetrazoline, 1-(2,6-diisopropylphenyl)-4-(2-cyclohexenyl)-5-thioxo-2-tetrazoline, 1-(2-methyl-6-isopropylphenyl)-4-sec.-butyl-5-thioxo-2-tetrazoline, 1-(2,6-diisopropyl-4-phenoxyphenyl)-4-cyclopropylmethyl-5-thioxo-2-tetrazoline, 1-(2,6-diisopropyl-4-benzylphenyl)-4-sec.-butyl-5-thioxo-2-tetrazoline, 1-(2,6-diisopropyl-4-benzylphenyl)-4-(2,2-dimethylpropyl)-5-thioxo-2-tetrazoline, 1-(2,6-diisopropyl-4-benzylphenyl)-4-isopropyl-5-thioxo-2-tetrazoline, 1-[2,6-diisopropyl-4-(2-fluorophenoxy)-phenyl]-4-isopropyl-5-thioxo-2-tetrazoline, 1-[2,6-diisopropyl-4-(1-phenethyl)-phenyl]-4-isopropyl-5-thioxo-2-tetrazoline, 1-(2-cyclopentyl-6-isopropyl-4-phenoxyphenyl)-4-isopropyl-5-thioxo-2-tetrazoline, 1(2-tert.-butyl-6-methylphenyl)-4-isopropyl-5-thioxo-2-tetrazoline, 1-(2-tert.-butyl-6-methylphenyl)-4-sec.-butyl-5-thioxo-2-tetrazoline, 1-(2-tert.-butyl-6-methylphenyl)-4-(2,2-dimethylpropyl)-5-thioxo-2-tetrazoline and 1-(2,6-diethylphenyl)-4-isopropyl-5-thioxo-2-tetrazoline.

13. An insecticidal or arachnidicidal composition which comprises at least an effective amount of a compound according to claim 1 and a carrier therefor.

14. A method of controlling insects and arachnids that are harmful to animals and plants which comprises treating said animals or plants or the locus thereof with an effective amount of a compound of formula I

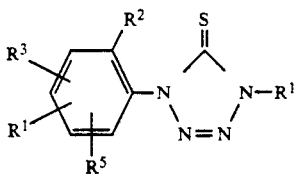

in which

R$^1$ is C$_1$-C$_8$alkyl, C$_3$-C$_6$alkenyl, C$_3$-C$_6$alkynyl, C$_3$-C$_6$-cycloalkyl, C$_5$-C$_6$-cycloalkenyl, C$_1$-C$_4$alkyl- or halo-substituted C$_3$-C$_6$cycloalkyl, C$_1$-C$_4$-alkyl- or halo-substituted C$_5$-C$_6$cycloalkenyl, halo-, C$_1$-C$_4$alkoxy- or phenyl-substituted C$_3$-C$_6$alkenyl, halo-, C$_1$-C$_4$alkoxy- or phenyl-substituted C$_3$-C$_8$alkynyl, or C$_1$-C$_8$alkyl that is substituted by halogen, C$_1$-C$_4$-alkoxy, C$_1$-C$_4$alkylthio, C$_1$-C$_4$alkoxycarbonyl, C$_3$-C$_6$cycloalkyl, phenyl, cyano, hydroxy, halophenyl, C$_1$-C$_4$alkylphenyl or by a heteroaromatic radical, R$^2$ is C$_1$-C$_6$alkyl, C$_2$-C$_6$alkenyl, C$_2$-C$_6$alkynyl, C$_3$-C$_6$-cycloalkyl, cyclopentenyl or cyclohexenyl, or is C$_1$-C$_6$alkyl that is substituted by halogen, by C$_1$-C$_4$alkoxy or by C$_1$-C$_4$alkylthio, each of R$^3$ and R$^4$, independently of the other, is hydrogen, halogen, C$_1$-C$_4$alkyl, C$_1$-C$_4$haloalkyl, C$_1$-C$_4$alkoxy, C$_1$-C$_4$alkylthio, C$_3$-C$_6$cycloalkyl, C$_2$-C$_4$alkenyl, C$_2$-C$_4$alkynyl, C$_2$-C$_6$alkoxyalkyl, C$_2$-C$_6$alkylthioalkyl, C$_1$-C$_4$cyanoalkyl, phenyl-C$_2$-C$_4$alkenyl or phenyl-C$_2$-C$_4$alkynyl, or R$^3$ and R$^4$ together are a —CH=CH—CH=CH—, —CH$_2$—CH=CH—, —(CH$_2$)$_4$—, —(CH$_2$)$_3$—, —O—CH$_2$—O—, —O—CH$_2$—CH$_2$—O—, —CH$_2$—O—CH$_2$—, —(CH$_2$)$_2$—CH=CH— or —CH$_2$—CH=CH—CH$_2$— bridge, each of which may be substituted by one or two C$_1$-C$_4$alkyl groups, and R$^5$ is hydrogen or a —Z—R$^6$ group in which R$^6$ is phenyl, naphthyl or pyridyl, or is phenyl, naphthyl or pyridyl each of which is substituted by one or two substituents selected from the group consisting of halogen, C$_1$-C$_4$alkyl, C$_1$-C$_4$alkoxy, C$_1$-C$_4$haloalkoxy, C$_1$-C$_4$haloalkyl, C$_1$-C$_4$alkylthio, C$_1$-C$_4$haloalkylthio, di-C$_1$-C$_4$alkylamino, nitro, cyano, C$_1$-C$_4$alkoxycarbonyl and C$_1$-C$_4$alkylcarbonyl, and Z is oxygen, sulfur, a direct bond, —NH—, —N(C$_1$-C$_2$alkyl)—, —N(CHO)—, —CH$_2$—, —CH(CH$_3$)— or —C(CH$_3$)$_2$—.

15. A method according to claim 14, wherein the pests are plant-destructive insects and arachnids.

* * * * *